(12) United States Patent
Snow

(10) Patent No.: US 11,844,500 B2
(45) Date of Patent: Dec. 19, 2023

(54) SEMI-AUTOMATIC BIOPSY NEEDLE DEVICE AND METHODS OF USE

(71) Applicant: Merit Medical Systems, Inc., South Jordan, UT (US)

(72) Inventor: Jeremy Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 22 days.

(21) Appl. No.: 15/980,116

(22) Filed: May 15, 2018

(65) Prior Publication Data

US 2018/0333145 A1    Nov. 22, 2018

Related U.S. Application Data

(60) Provisional application No. 62/536,687, filed on Jul. 25, 2017, provisional application No. 62/508,844, filed on May 19, 2017.

(51) Int. Cl.
*A61B 10/02* (2006.01)
*A61B 90/00* (2016.01)

(52) U.S. Cl.
CPC .. *A61B 10/0275* (2013.01); *A61B 2010/0208* (2013.01); *A61B 2090/031* (2016.02)

(58) Field of Classification Search
CPC ........ A61B 10/0275; A61B 2010/0208; A61B 2090/031; A01D 34/34; F16H 2061/2869
USPC ...................................................... 600/567
See application file for complete search history.

(56) References Cited

U.S. PATENT DOCUMENTS

| | | |
|---|---|---|
| 737,293 A | 8/1903 | Summerfeldt |
| 1,585,934 A | 12/1923 | Muir |
| 1,663,761 A | 2/1927 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hayden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |

(Continued)

FOREIGN PATENT DOCUMENTS

| | | |
|---|---|---|
| DE | 2848314 | 10/1979 |
| DE | 3924291 | 1/1991 |

(Continued)

OTHER PUBLICATIONS

International Search Report and Written Opinion dated Sep. 4, 2018 for PCT/US2018/033188.

(Continued)

*Primary Examiner* — Daniel L Cerioni
(74) *Attorney, Agent, or Firm* — Dorsey & Whitney LLP

(57) ABSTRACT

A biopsy needle device is disclosed. The biopsy needle device may be configured to be advanced to a predetermined tissue sample, collect and sever the tissue sample utilizing an actuator comprising a linear displacement mechanism, and extract the tissue sample from a body tissue of a patient.

5 Claims, 22 Drawing Sheets

(56) References Cited

U.S. PATENT DOCUMENTS

| | | |
|---|---|---|
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,416,305 A | 11/1983 | Commette et al. |
| 4,445,509 A | 5/1984 | Auth |
| 4,490,137 A | 12/1984 | Moukheibir |
| 4,549,554 A | 10/1985 | Markham |
| 4,557,265 A | 12/1985 | Anderson |
| 4,577,629 A | 3/1986 | Martinez |
| 4,589,414 A | 5/1986 | Yoshida et al. |
| 4,598,710 A | 7/1986 | Kleinberg et al. |
| 4,603,694 A | 8/1986 | Wheeler |
| 4,605,011 A | 8/1986 | Naslund |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,662,869 A | 5/1987 | Wright |
| 4,678,459 A | 7/1987 | Onik et al. |
| 4,683,885 A | 8/1987 | Hutterer et al. |
| 4,696,298 A | 9/1987 | Higgins et al. |
| 4,702,260 A | 10/1987 | Wang |
| 4,708,147 A | 11/1987 | Haaga |
| 4,776,346 A | 10/1988 | Beraha et al. |
| 4,844,087 A | 7/1989 | Garg |
| 4,850,354 A | 7/1989 | McGurk-Burleson et al. |
| 4,893,635 A | 1/1990 | De Groot et al. |
| 4,907,598 A | 3/1990 | Bauer |
| RE33,258 E | 7/1990 | Onik et al. |
| 4,940,061 A | 7/1990 | Terwilliger et al. |
| 4,944,308 A | 7/1990 | Ang |
| 4,952,817 A | 8/1990 | Bolan et al. |
| 4,958,625 A | 9/1990 | Bates et al. |
| 4,967,762 A | 11/1990 | Devries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,225,763 A | 7/1993 | Krohn et al. |
| 5,226,910 A | 7/1993 | Kajiyama et al. |
| 5,234,000 A | 8/1993 | Hakky et al. |
| 5,236,334 A | 8/1993 | Bennett |
| 5,249,583 A | 10/1993 | Mallaby |
| 5,269,791 A | 12/1993 | Mayzels et al. |
| 5,282,476 A | 2/1994 | Terwilliger |
| 5,282,477 A | 2/1994 | Bauer |
| 5,284,472 A | 2/1994 | Sussman et al. |
| 5,292,327 A | 3/1994 | Dodd et al. |
| 5,306,260 A | 4/1994 | Kanner |
| 5,324,306 A | 6/1994 | Makower et al. |
| 5,334,183 A | 8/1994 | Wuchinich |
| 5,336,229 A | 8/1994 | Noda |
| 5,368,029 A | 11/1994 | Holcombe et al. |
| 5,368,045 A | 11/1994 | Clement et al. |
| 5,395,313 A | 3/1995 | Naves et al. |
| 5,400,798 A | 3/1995 | Baran |
| 5,409,013 A | 4/1995 | Clement |
| 5,439,474 A | 8/1995 | Li |
| 5,441,510 A | 8/1995 | Simpson et al. |
| 5,449,001 A | 9/1995 | Terwilliger |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,505,210 A | 4/1996 | Clement |
| 5,511,556 A | 4/1996 | De Santis |
| 5,526,822 A | 6/1996 | Burbank et al. |
| 5,527,322 A | 6/1996 | Clement |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,562,685 A | 10/1996 | Mollenauer et al. |
| 5,564,436 A | 10/1996 | Hakky et al. |
| 5,569,277 A | 10/1996 | Evans et al. |
| 5,569,284 A | 10/1996 | Young et al. |
| 5,575,293 A | 11/1996 | Miller et al. |
| 5,582,616 A | 12/1996 | Bolduc et al. |
| 5,591,170 A | 1/1997 | Spievack et al. |
| 5,601,585 A | 2/1997 | Banik et al. |
| 5,602,449 A | 2/1997 | Krause et al. |
| 5,617,874 A | 4/1997 | Baran |
| 5,643,304 A | 7/1997 | Schechter et al. |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | De Santis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | De Santis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |

(56) References Cited

U.S. PATENT DOCUMENTS

| | | |
|---|---|---|
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,361,504 B1 | 3/2002 | Shin |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,779 B2 | 4/2003 | Viola et al. |
| 6,585,664 B2 | 7/2003 | Burdoff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,025,732 B2 | 4/2006 | Thompson et al. |
| 7,048,694 B2 | 5/2006 | Mark et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner et al. |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 * | 4/2009 | Viola ............... A61B 10/0275 600/564 |
| 7,517,321 B2 | 4/2009 | Mccullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibner |
| 7,883,476 B2 | 2/2011 | Miller et al. |
| 8,251,917 B2 | 8/2012 | Almazan |
| 9,474,527 B1 | 10/2016 | Knodel et al. |
| 2001/0005778 A1 | 6/2001 | Ouchi |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0077646 A1 | 6/2002 | Truwit et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0151822 A1 | 10/2002 | Brudorff et al. |
| 2002/0156395 A1 | 10/2002 | Stephens et al. |
| 2003/0114875 A1 | 6/2003 | Sjostrom |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0133124 A1 | 7/2004 | Bates et al. |
| 2004/0167427 A1 | 8/2004 | Quick et al. |
| 2004/0186393 A1 | 9/2004 | Leigh et al. |
| 2004/0215103 A1 | 10/2004 | Mueller et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |

(56) References Cited

U.S. PATENT DOCUMENTS

| | | |
|---|---|---|
| 2006/0074346 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | Mccullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258953 A1 | 11/2006 | Lee |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0068990 A1* | 3/2007 | Shelton ............ A61B 17/07207 227/175.1 |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarina |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bichenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0223904 A1* | 9/2008 | Marczyk .......... A61B 17/07207 227/176.1 |
| 2008/0228104 A1 | 9/2008 | Uber et al. |
| 2008/0232604 A1 | 9/2008 | Dufresne et al. |
| 2008/0234715 A1 | 9/2008 | Pescue et al. |
| 2008/0281225 A1 | 11/2008 | Spero et al. |
| 2008/0281226 A1 | 11/2008 | Peters |
| 2008/0287826 A1 | 11/2008 | Videbaek et al. |
| 2008/0306404 A1 | 12/2008 | Ronald |
| 2008/0306406 A1 | 12/2008 | Thompson et al. |
| 2008/0308607 A1 | 12/2008 | Timm et al. |
| 2008/0312554 A1 | 12/2008 | Garrison |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0088666 A1 | 4/2009 | Miller et al. |
| 2009/0125062 A1 | 5/2009 | Arnin |
| 2009/0137927 A1 | 5/2009 | Miller |
| 2009/0163870 A1 | 6/2009 | Flagle et al. |
| 2009/0171243 A1 | 7/2009 | Hibner et al. |
| 2009/0204021 A1 | 8/2009 | Shabaz et al. |
| 2009/0082695 A1 | 9/2009 | Whitehead |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0114031 A1 | 5/2010 | Jarial et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0071391 A1 | 3/2011 | Speeg |
| 2011/0152715 A1 | 6/2011 | Delap et al. |
| 2011/0160611 A1 | 6/2011 | Ritchart et al. |
| 2011/0224577 A1 | 9/2011 | Park |
| 2011/0237976 A1 | 9/2011 | Weitzel et al. |
| 2011/0313316 A1 | 12/2011 | Ranpura et al. |
| 2012/0022397 A1 | 1/2012 | Jarial |
| 2012/0116248 A1 | 5/2012 | Mcweeney et al. |
| 2012/0130274 A1 | 5/2012 | Persat |
| 2012/0197157 A1 | 8/2012 | Ryan et al. |
| 2012/0215130 A1 | 8/2012 | Field et al. |
| 2012/0253228 A1 | 10/2012 | Schembre et al. |
| 2013/0046316 A1 | 2/2013 | Sullivan et al. |
| 2014/0100448 A1 | 4/2014 | Neilan |
| 2014/0207021 A1 | 7/2014 | Snow |
| 2014/0228705 A1 | 8/2014 | Linderman et al. |
| 2014/0276205 A1 | 9/2014 | Miller et al. |
| 2014/0296741 A1 | 10/2014 | Austen |
| 2014/0302462 A1* | 10/2014 | Vatcher ................ A63G 31/16 434/55 |
| 2014/0371585 A1 | 12/2014 | Thompson et al. |
| 2015/0119916 A1* | 4/2015 | Dietz ............ A61B 17/320068 606/169 |
| 2015/0201917 A1 | 7/2015 | Snow |
| 2015/0342580 A1 | 12/2015 | Clancy |
| 2016/0030016 A1 | 2/2016 | Mcweeney et al. |
| 2016/0081678 A1 | 3/2016 | Kappel et al. |
| 2016/0128784 A1 | 5/2016 | Ahari |
| 2016/0324508 A1 | 11/2016 | Duggan et al. |
| 2016/0354066 A1 | 12/2016 | Asaoka et al. |
| 2018/0333146 A1 | 11/2018 | Hallisey et al. |
| 2018/0333147 A1 | 11/2018 | Snow et al. |
| 2019/0110779 A1* | 4/2019 | Gardner ................ A61B 10/02 |
| 2021/0093305 A1 | 4/2021 | Peliks et al. |

FOREIGN PATENT DOCUMENTS

| | | |
|---|---|---|
| DE | 4120329 | 1/1992 |
| DE | 4041614 | 10/1992 |
| DE | 2453058 | 5/1996 |
| DE | 10034297 | 4/2001 |
| DE | 10026303 | 2/2002 |
| DE | 20209525 | 11/2002 |
| DE | 10235480 | 2/2004 |
| EP | 0433717 | 6/1991 |
| EP | 541377 | 5/1993 |
| EP | 0890339 | 1/1999 |
| EP | 0995400 | 4/2000 |
| EP | 1074271 | 2/2001 |
| EP | 1520518 | 4/2005 |
| EP | 1579809 | 9/2005 |
| EP | 1665958 | 6/2006 |
| EP | 2095772 | 2/2009 |
| EP | 2106750 | 10/2009 |
| FR | 1345429 | 12/1963 |

(56) References Cited

FOREIGN PATENT DOCUMENTS

| | | |
|---|---|---|
| FR | 2739293 | 4/1997 |
| GB | 2018601 | 10/1979 |
| GB | 2038640 | 12/1979 |
| JP | H10508504 | 8/1998 |
| JP | 2005530554 | 10/2005 |
| JP | 2006509545 | 3/2006 |
| JP | 2006528907 | 12/2006 |
| JP | 2007502159 | 2/2007 |
| SU | 1454457 | 1/1989 |
| WO | 199314700 | 8/1993 |
| WO | 199416181 | 7/1994 |
| WO | 199428801 | 12/1994 |
| WO | 199628097 | 9/1996 |
| WO | 199825522 | 6/1998 |
| WO | 199831285 | 7/1998 |
| WO | 199835615 | 8/1998 |
| WO | 199846290 | 10/1998 |
| WO | 199915079 | 4/1999 |
| WO | 199933501 | 7/1999 |
| WO | 200004832 | 2/2000 |
| WO | 200030546 | 6/2000 |
| WO | 200059378 | 10/2000 |
| WO | 200172230 | 10/2001 |
| WO | 200222023 | 3/2002 |
| WO | 200232318 | 4/2002 |
| WO | 2002069808 | 9/2002 |
| WO | 20040757719 | 9/2004 |
| WO | 2005013830 | 2/2005 |
| WO | 2006015302 | 2/2006 |
| WO | 2007047128 | 4/2007 |
| WO | 2007095330 | 8/2007 |
| WO | 2007112751 | 10/2007 |
| WO | 2008021687 | 2/2008 |
| WO | 2008024684 | 2/2008 |
| WO | 2008040812 | 4/2008 |
| WO | 2008131362 | 10/2008 |
| WO | 2010107424 | 9/2010 |
| WO | 2013158072 | 10/2013 |
| WO | 2014081812 | 5/2014 |

OTHER PUBLICATIONS

International Search Report and Written Opinion dated Sep. 11, 2018 for PCT/US2018/032789.
International Search Report and Written Opinion dated Sep. 17, 2018 for PCT/US2018/033235.
International Search Report and Written Opinion dated Jul. 2, 2009 for PCT/KR2009/006741.
Office Action dated May 12, 2020 for U.S. Appl. No. 15/982,624.
Office Action dated May 12, 2020 for U.S. Appl. No. 15/982,777.
European Search Report dated Jan. 26, 2021 for EP18801552.3.
European Search Report dated Feb. 1, 2021 for EP18802126.5.
European Search Report dated Feb. 4, 2021 for EP18801940.0.
Office Action dated Nov. 17, 2020 for U.S. Appl. No. 15/982,624.
Office Action dated Nov. 27, 2020 for U.S. Appl. No. 15/982,777.
European Search Report dated May 7, 2021 for EP18801940.0.
Notice of Allowance dated Jul. 9, 2021 for U.S. Appl. No. 15/982,624.
Notice of Allowance dated Aug. 25, 2021 for U.S. Appl. No. 15/965,109.
Office Action dated Aug. 9, 2021 for U.S. Appl. No. 15/982,777.
Office Action dated May 24, 2022 for U.S. Appl. No. 15/982,777.
Office Action dated Nov. 14, 2022 for U.S. Appl. No. 15/982,777.
Office Action dated Feb. 14, 2022 for U.S. Appl. No. 15/982,777.
Notice of Allowance dated Jul. 5, 2023 for U.S. Appl. No. 15/982,777.

* cited by examiner

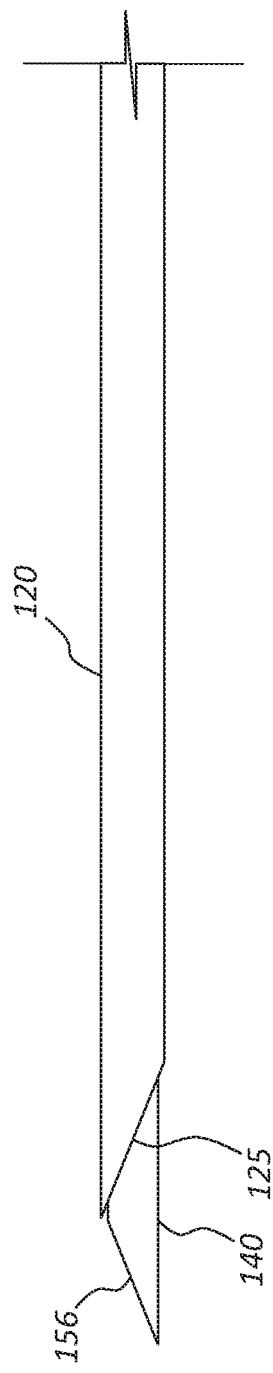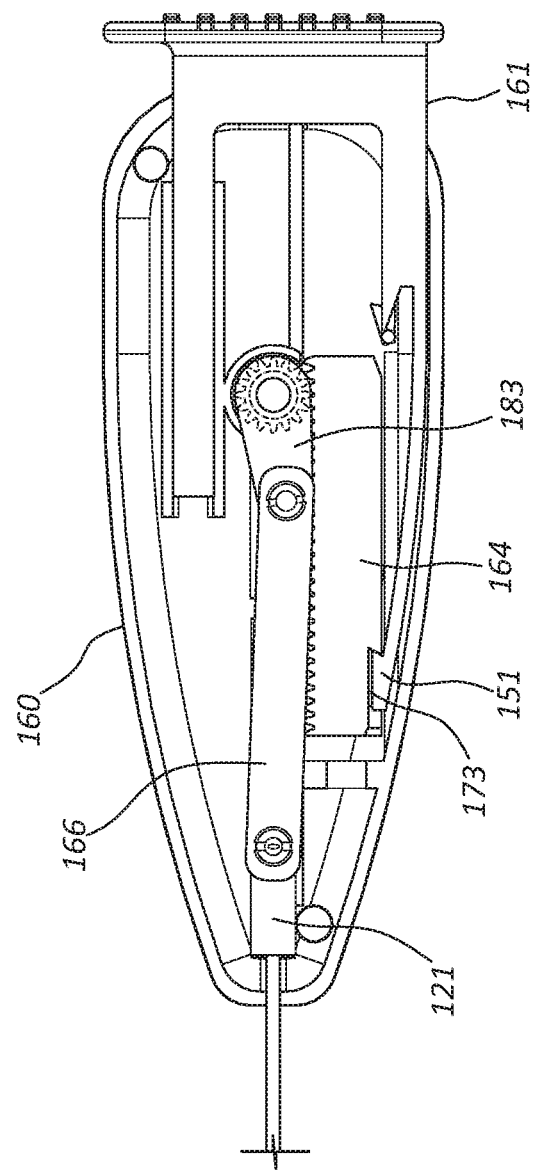

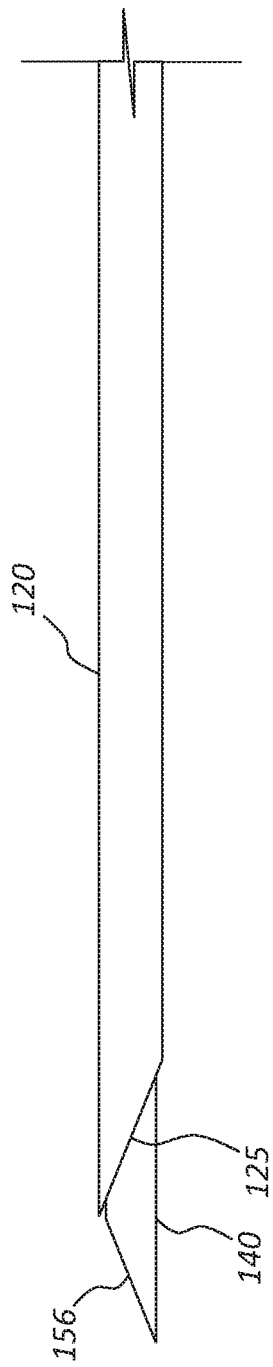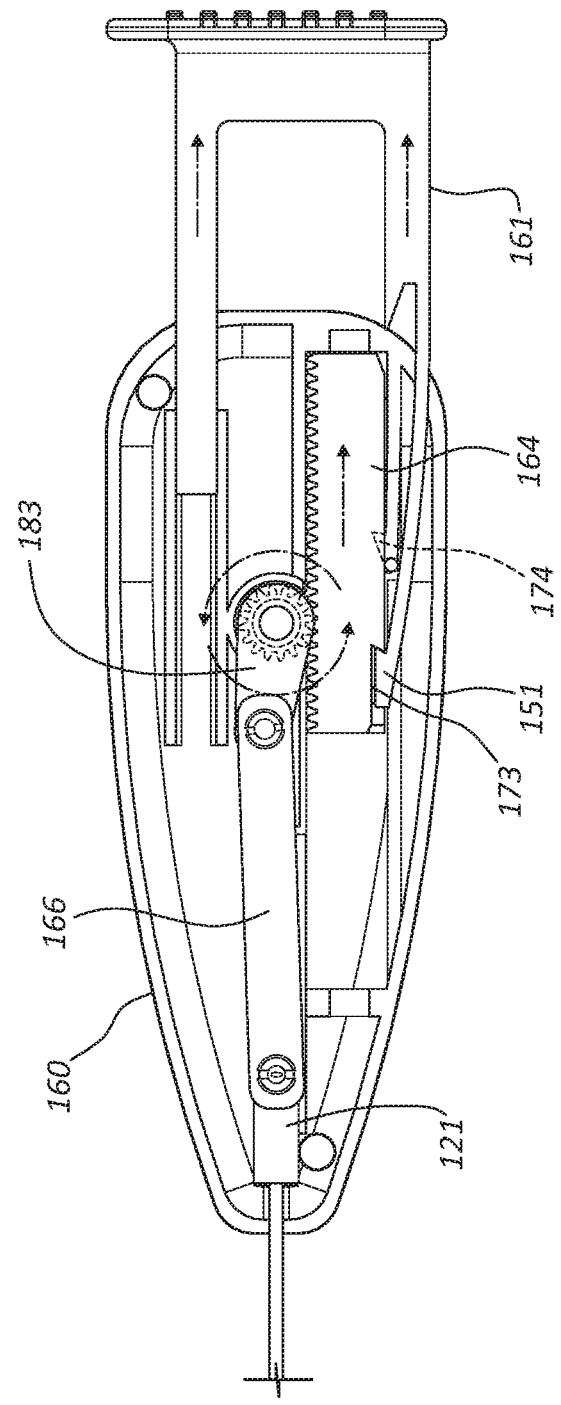

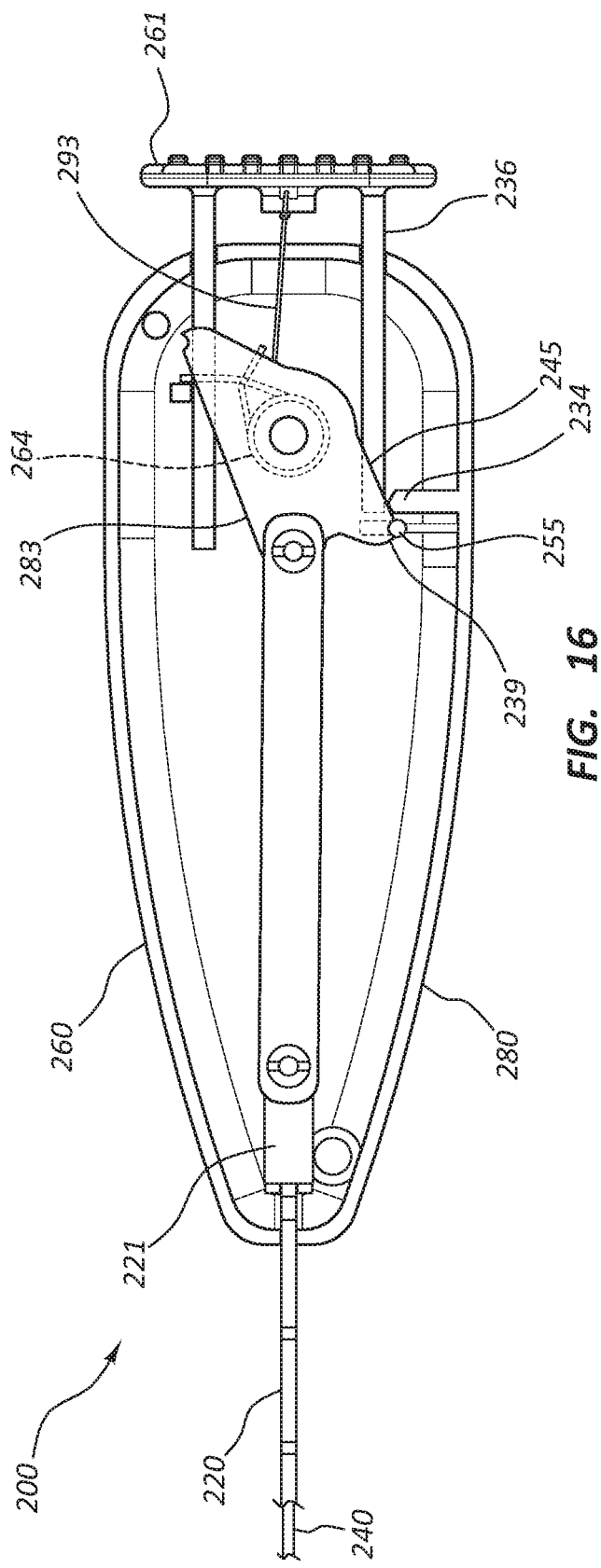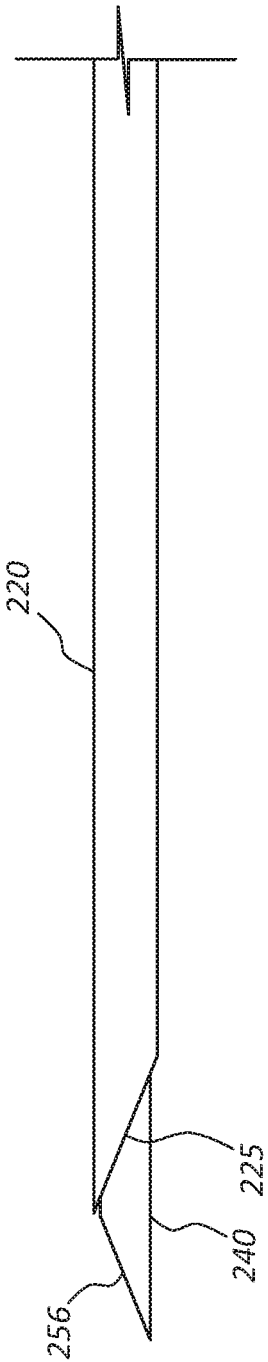
FIG. 16
FIG. 16A

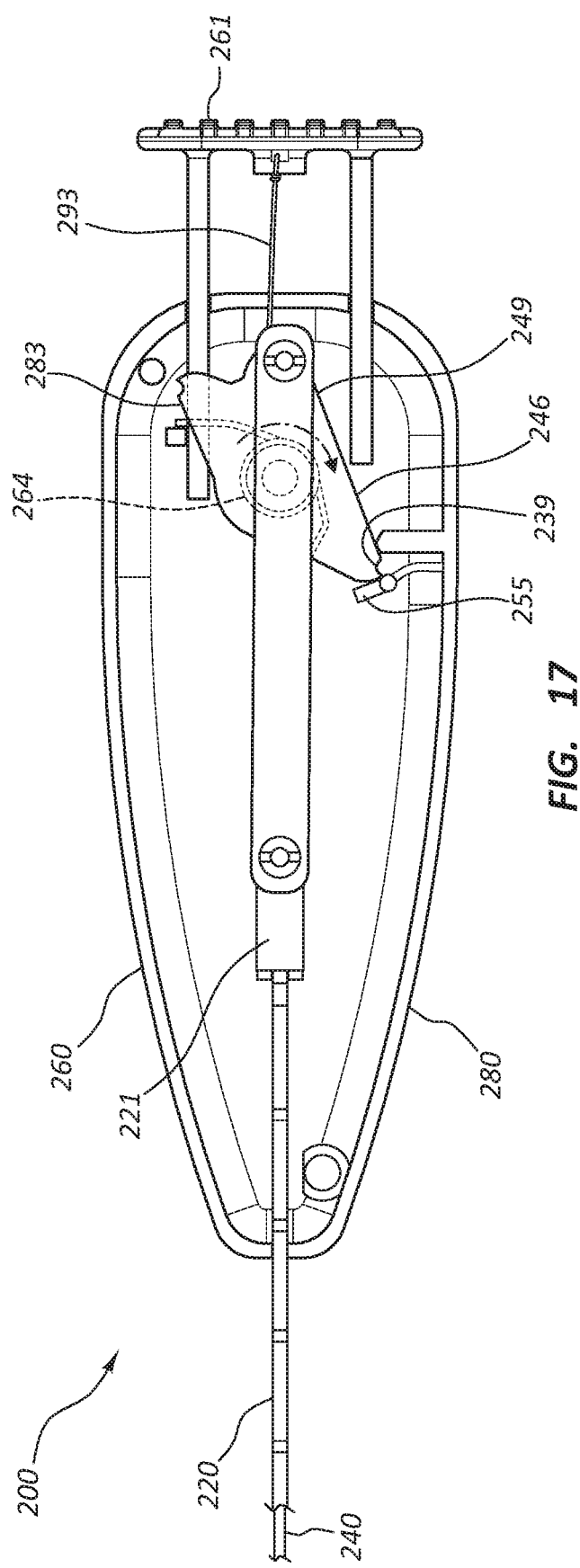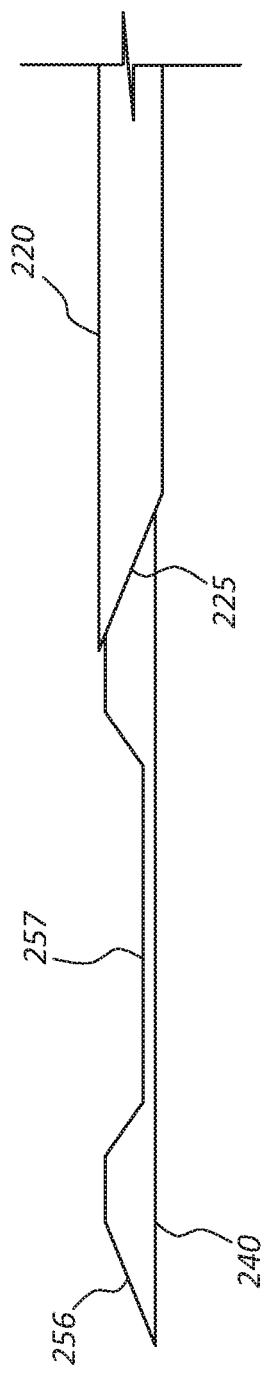
FIG. 17
FIG. 17A

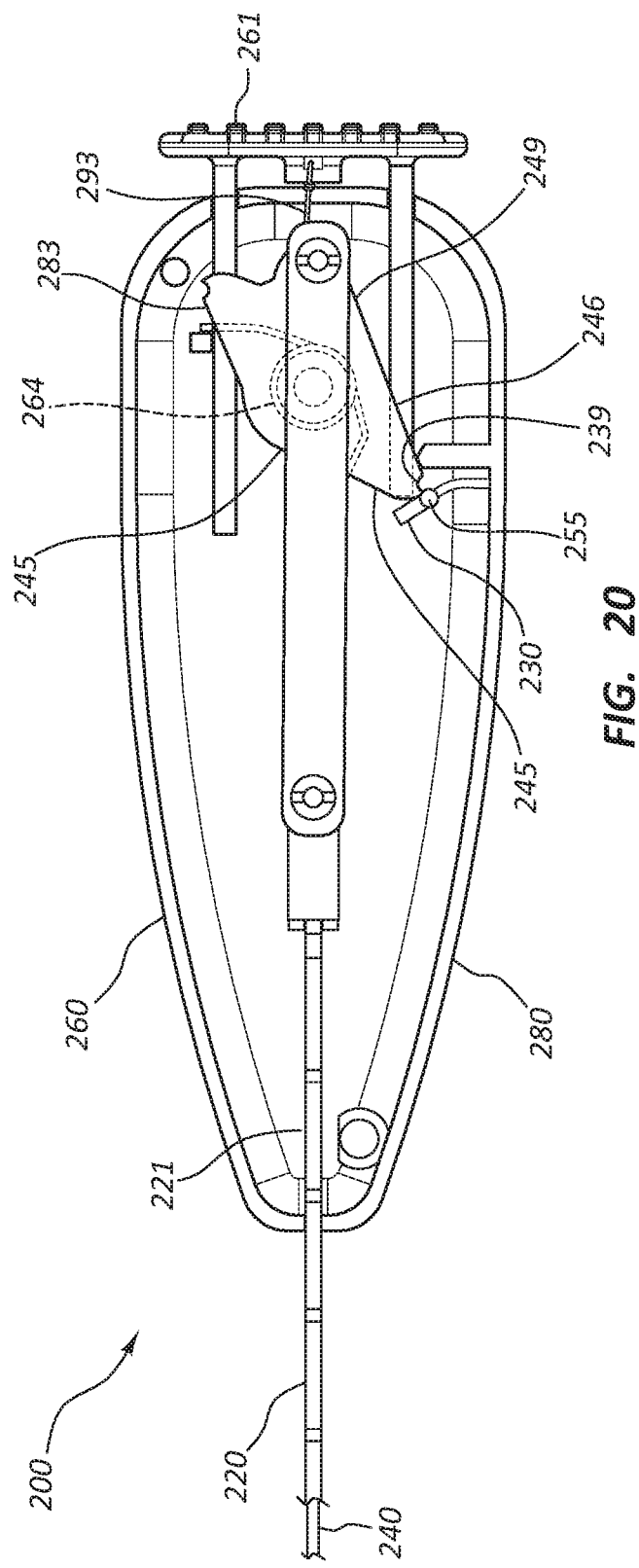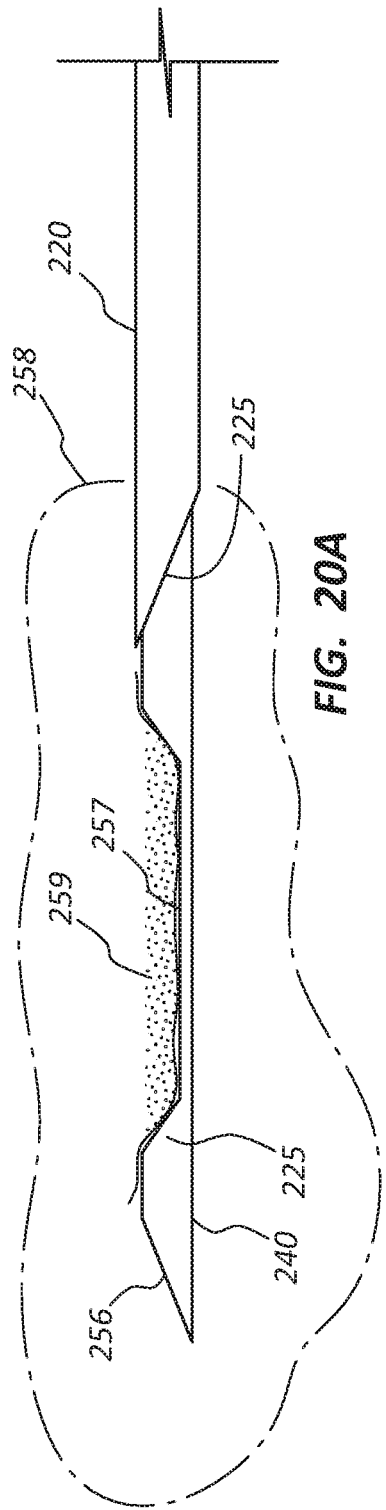
FIG. 20
FIG. 20A

SEMI-AUTOMATIC BIOPSY NEEDLE DEVICE AND METHODS OF USE

RELATED APPLICATIONS

This application claims priority to U.S. Provisional Application No. 62/508,844, filed on May 19, 2017 and titled, "Semi-Automatic Biopsy Needle and Methods of Use," and U.S. Provisional Application No. 62/536,687, filed on Jul. 25, 2017 and titled, "Semi-Automatic Biopsy Needle and Methods of Use," both of which are hereby incorporated by reference in their entireties.

TECHNICAL FIELD

The present disclosure relates generally to medical devices. More specifically, the present disclosure relates to biopsy needle assemblies configured for use with tissue biopsy devices, including needle assemblies configured to decrease, minimize, or eliminate axial translation of the needle assemblies at a tissue sample collection site.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 2A is a detail view of a distal end portion of the cannula of FIG. 2 taken from detail line 2A.

FIG. 3A is a detail view of a distal end portion of the trocar of FIG. 3 taken from detail line 3A.

FIG. 6 is a schematic representation of portions of the biopsy needle device actuator of FIG. 1 in a first configuration.

FIG. 6A is a schematic representation of portions of the cannula and trocar of the biopsy needle device of FIG. 1 in the first configuration correlating to FIG. 6.

FIG. 8 is a schematic representation of portions of the biopsy needle device actuator of FIG. 1 in a third configuration.

FIG. 8A is a schematic representation of portions of the cannula and trocar of the biopsy needle device of FIG. 1 in the third configuration correlating to FIG. 8.

FIG. 16 is a schematic representation of portions of the biopsy needle device actuator of FIG. 12 in a first configuration.

FIG. 16A is a schematic representation of portions of the cannula and trocar of the biopsy needle device of FIG. 12 in the first configuration correlating to FIG. 16.

FIG. 17 is a schematic representation of portions of the biopsy needle device actuator of FIG. 12 in a second configuration.

FIG. 17A is a schematic representation of portions of the cannula and trocar of the biopsy needle device of FIG. 12 in the second configuration correlating to FIG. 17.

FIG. 20 is a schematic representation of portions of the biopsy needle device actuator of FIG. 12 in a fifth configuration.

FIG. 20A is a schematic representation of portions of the cannula and trocar of the biopsy needle device of FIG. 12 in the fifth configuration correlating to FIG. 20.

DETAILED DESCRIPTION

Figure 1:
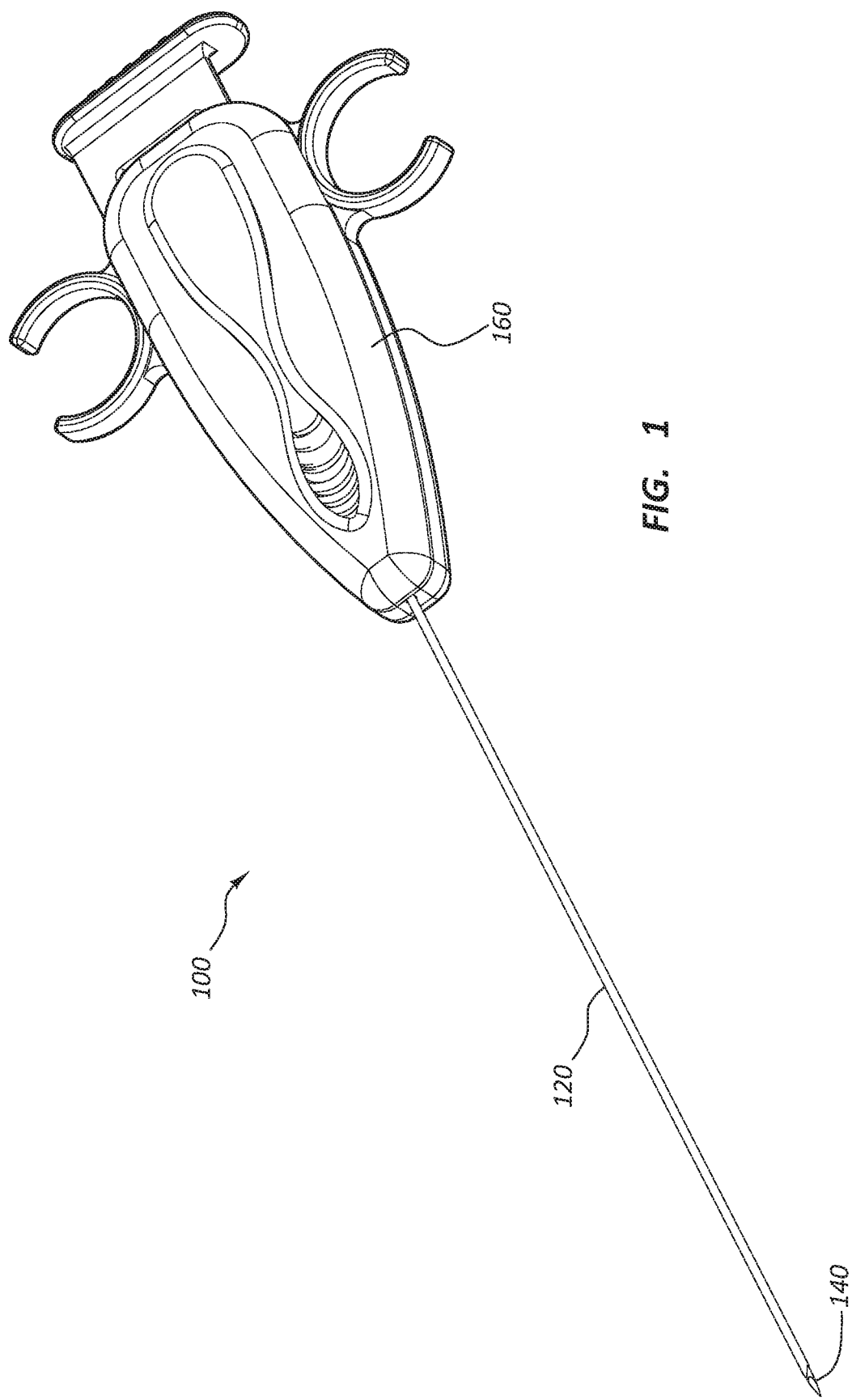
FIG. 1 is a perspective view of a biopsy needle device.

Tissue biopsy devices may be configured to retrieve tissue samples from various locations within a patient's body. For example, a biopsy device may comprise a biopsy needle device, or needle assembly, including tubular members, needles, trocars, cutting styli, styli, cannula, and/or other components configured to access and sever a tissue sample in a medical procedure commonly referred to as Core Needle Biopsy. The biopsy needle device may be advanced to a location within the body through the skin of the patient (percutaneous access), through an open incision, or may be advanced through a body lumen or other structure. A portion of the biopsy needle device may be advanced into a lesion or target tissue. Another portion of the biopsy needle device may then be advanced into the lesion or target tissue to sever a tissue sample from the lesion or target tissue. The biopsy needle device may then be withdrawn from the patient, and the tissue sample extracted from the needle device for analysis. Furthermore, a biopsy needle device may comprise a handle or actuator configured to axially displace or deflect at least a portion of the biopsy needle device such that the biopsy needle device cuts or severs the targeted tissue sample.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. For example, as specifically applied to the needle portion of the biopsy needle device, the proximal end of the needle refers to the end nearest the handle or actuator, and the distal end refers to the opposite end: the end that may be inserted into a patient.

"Tissue" is used in its broadest sense, to refer to any tissue or substance within a human body.

FIGS. 1-22A illustrate different views of a biopsy needle device and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 is a perspective view of a biopsy needle device 100. As illustrated, the biopsy needle device 100 may comprise an outer member or cannula 120, an inner member or trocar 140, and an actuator 160.

Figure 2:
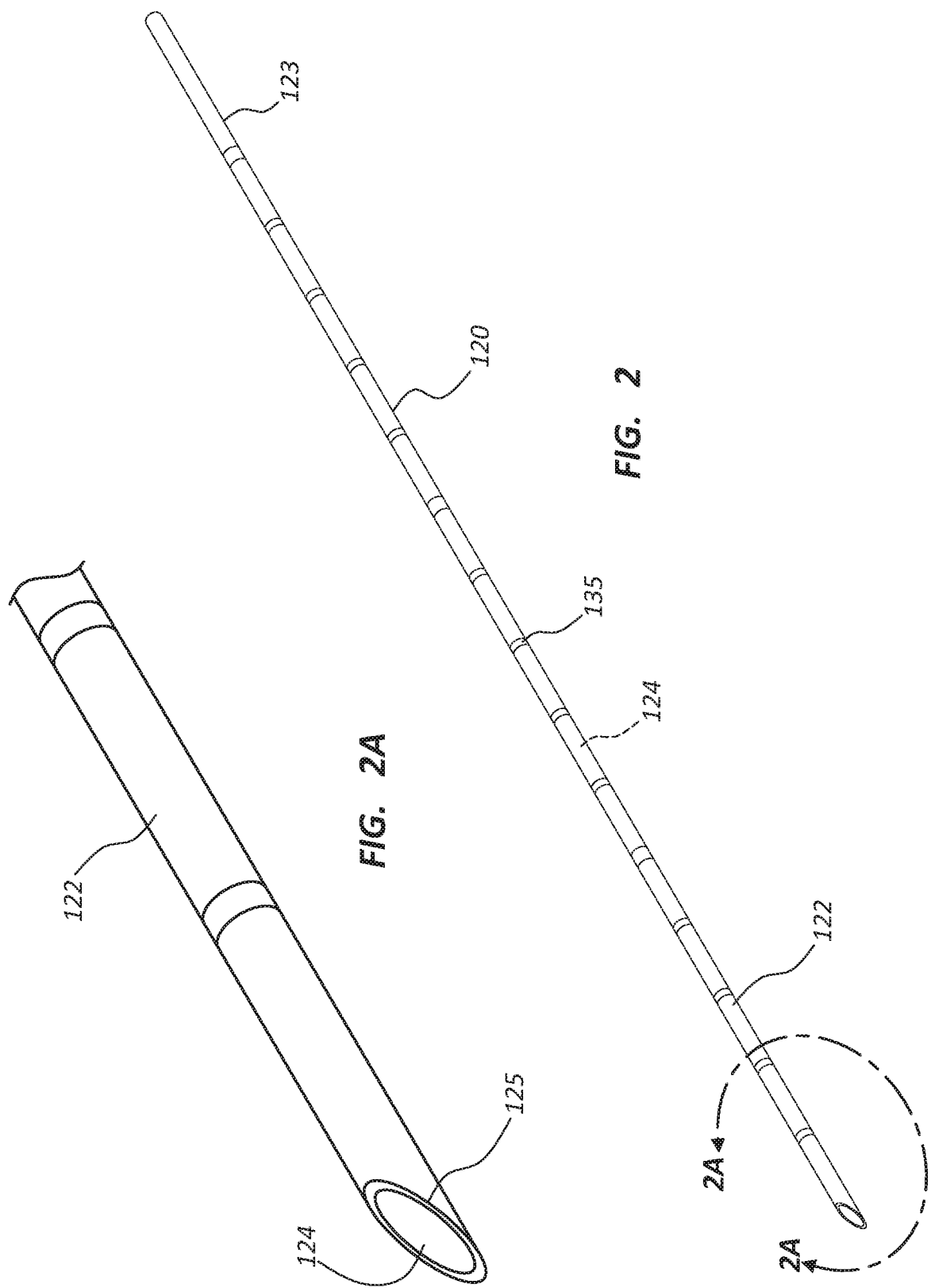
FIG. 2 is a perspective view of a cannula of the biopsy needle device of FIG. 1.

FIG. 2 is a perspective view of the cannula 120 of FIG. 1, and FIG. 2A is a detail view of a distal end portion 122 of the cannula 120 of FIG. 2 taken through detail line 2A. Referring now to FIGS. 2-2A, in some embodiments the cannula 120 may comprise an elongate tube having the distal end portion 122, a proximal end portion 123 and a lumen 124. The cannula 120 may range in diameter from 22 gauge to 8 gauge and including from 20 gauge to 14 gauge. The lumen 124 of the cannula 120 may be sized to accommodate the positioning of the trocar 140 within the lumen 124. The length of the cannula 120 may range from 5 cm to 100 cm and including from 10 cm to 25 cm. The cannula 120 may be manufactured from a medical-grade stainless steel material.

In some embodiments the proximal end portion 123 of the cannula 120 may be configured to be fixedly coupled to a cannula hub 121 of the actuator (160 of FIG. 1) such that the proximal end of the lumen 124 is open to allow for passage of the trocar 140 into the lumen 124. The cannula 120 may be fixedly coupled to the cannula hub 121 using any suitable techniques including bonding, welding, overmolding, press fit, etc. The outside surface of the proximal end portion 123 of the cannula 120 may be modified to enhance the coupling of the cannula 120 to the cannula hub 121. For example, the surface may be chemically or mechanically etched or textured to roughen the surface in order to enhance the adhesion of an adhesive or plastic. Alternatively, the surface may be chemically modified to enhance the adhesion of the adhesive or plastic.

The distal end portion 122 of the cannula 120 may comprise a bevel 125. The bevel 125 may be configured to cut or sever tissue as the cannula 120 slides along the longitudinal axis of the trocar 140. The bevel 125 may have an angle of from 5 degrees to 180 degrees and including from 25 degrees to 30 degrees. The bevel may be configured to have other undulating surfaces configured to be sharp to cut or sever tissue. The edges of the bevel 125 may be sharp and may be configured to cut or sever tissue.

In certain embodiments the cannula 120 may comprise a plurality of indicia 135 configured to indicate to the practitioner a distance that the cannula 120 and the trocar 140 have advanced into a body tissue (for clarity, not all indicia 135 are labeled). For example, each indicium 135 may be positioned 1 cm apart; thus, if the practitioner displaces the cannula 120 and the trocar 140 into a body tissue up to the third indicium 135 from a distal end portion 142 of the trocar 140, it may indicate to the practitioner that approximately 3 cm of the trocar 140 and cannula 120 has been displaced into the body tissue. In some embodiments, the indicia 135 may comprise a plurality of substantially evenly spaced annular lines, marks, or grooves on an outside surface of the cannula 120. In certain embodiments, the indicia 135 may comprise a plurality of tick marks, or the indicia 135 may not be evenly spaced.

In certain embodiments, a portion or portions of at least one of the components of the biopsy needle device 100, including, but not limited to, the cannula 120 and/or the trocar 140, may comprise a radiopaque material and/or an echogenic material. A radiopaque material (for example, in combination with computed tomography or x-ray) may aid the practitioner in directing or displacing the biopsy needle device 100 to a desired or predetermined position within the body tissue of the patient. Bismuth, gold, or other radiopaque materials, alone or in combination, may be used. An echogenic material or surface (for example, in combination with ultrasound) may analogously aid the practitioner in directing or displacing the needle device 100 to a desired or predetermined position within the body tissue of the patient. Surface disruptions such as texturing, grooves, dimples, or a combination of materials may also be used.

Figure 3:
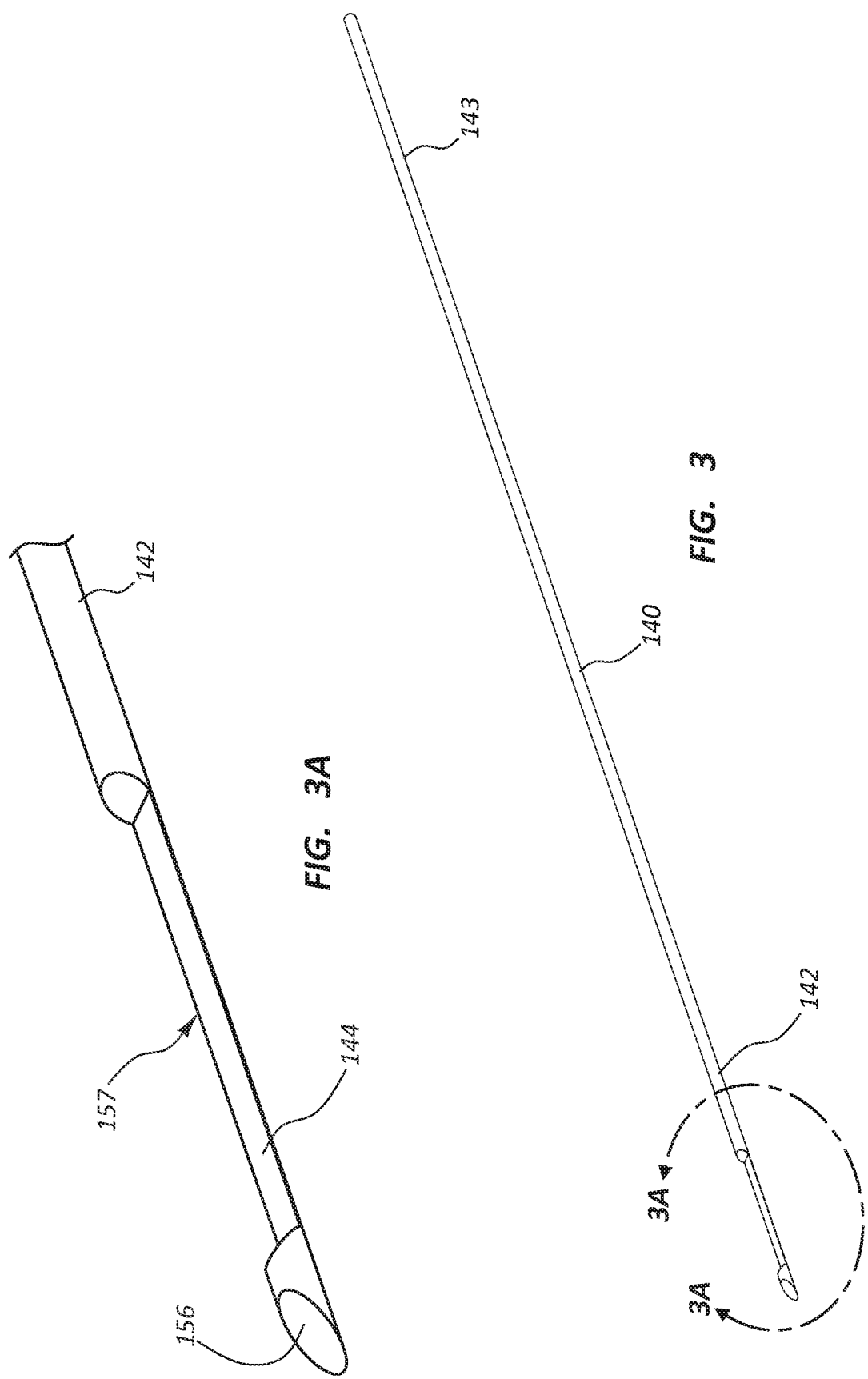
FIG. 3 is a perspective view of a trocar of the biopsy needle device of FIG. 1.

FIG. 3 is a perspective view of the trocar 140 of FIG. 1, and FIG. 3A is a detail view of the distal end portion 142 of the trocar 140 of FIG. 3 taken from detail line 4A. Referring to FIGS. 3-3A, in some embodiments the trocar 140 may comprise an elongate rod having the distal end portion 142 and a proximal end portion 143. Alternatively, the trocar 140 may comprise an elongate tube having a lumen. The trocar 140 outer diameter may be configured such that the trocar 140 may be slidingly disposed within the lumen 124 of the cannula 120. The trocar 140 may range in diameters and lengths to match the cannula for optimized tissue cutting. The trocar 140 may be manufactured from a medical-grade stainless steel material.

The distal end portion 142 of the trocar 140 may comprise a bevel 156 and a notch 157. The bevel 156 may be configured to penetrate tissue. The bevel 156 may be configured as any type of tissue-penetrating bevel utilized in medical devices comprising a needle or trocar. For example, the bevel 156 may be of a type such as Tri-cut, Whitacre, pencil point, Seldinger, Sprotte, etc.

In some embodiments the notch 157 may be located proximal of the bevel 156. The length of the notch 157 may range from 5 millimeters to 35 millimeters and including embodiments where it is 20 millimeters. The depth of the notch 157 may be approximately 50% of the outer diameter of the trocar 140. A base 144 of the notch 157 may be planar. Alternatively, the notch 157 may comprise a trough having side walls and a concave base such as would be created by removing a portion of a wall of a hollow trocar. The notch 157 may be configured to capture and retain the tissue sample cut or severed by the cannula (120 of FIG. 2). For example, the trocar 140 may be inserted into the target tissue or lesion. A portion of the target tissue or lesion may collapse into the notch 157. The cannula (120 of FIG. 2) may then be advanced over the trocar 140, cutting or severing the portion of the target tissue or the lesion from the surrounding tissue. The cut or severed tissue sample may be captured and retained within the notch 157 and the cannula lumen (124 of FIG. 4).

Referring to FIGS. 1, 3, and 3A, in some embodiments the proximal end portion 143 of the trocar 140 may be configured to be fixedly coupled to the actuator 160. The trocar 140 may be fixedly coupled to the actuator 160 using any suitable technique including bonding, welding, overmolding, press fit, etc. The outside surface of the proximal end portion 143 of the trocar 140 may be modified to enhance the coupling of the trocar 140 to the actuator 160. For example, the surface may be chemically or mechanically etched or textured to roughen the surface in order to enhance the adhesion of an adhesive or plastic. Alternatively, the surface may be chemically modified to enhance the adhesion of the adhesive or plastic.

Figure 4:
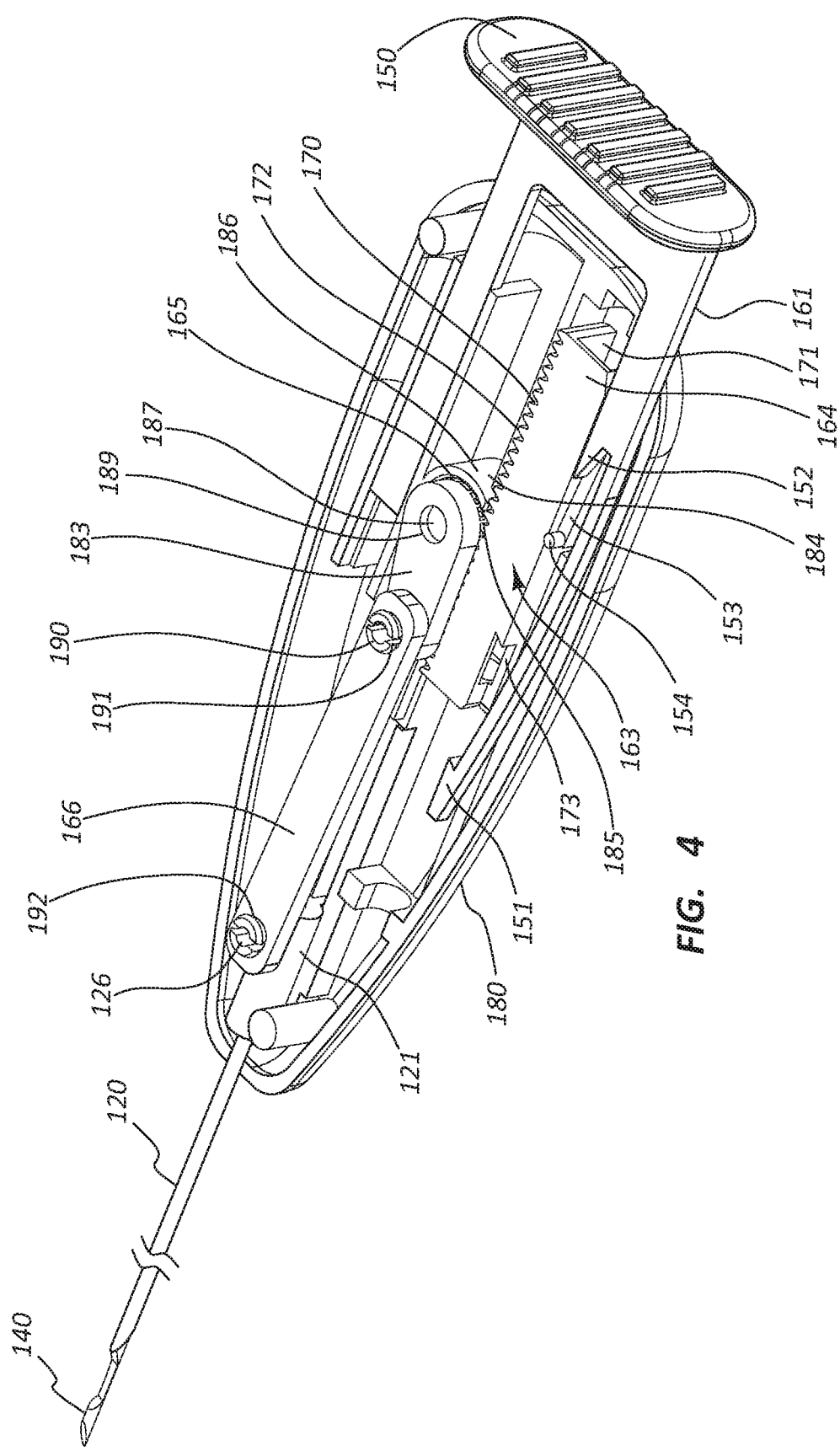
FIG. 4 is a perspective view of an actuator of the biopsy needle device of FIG. 1, shown with a housing lid removed.
Figure 5:
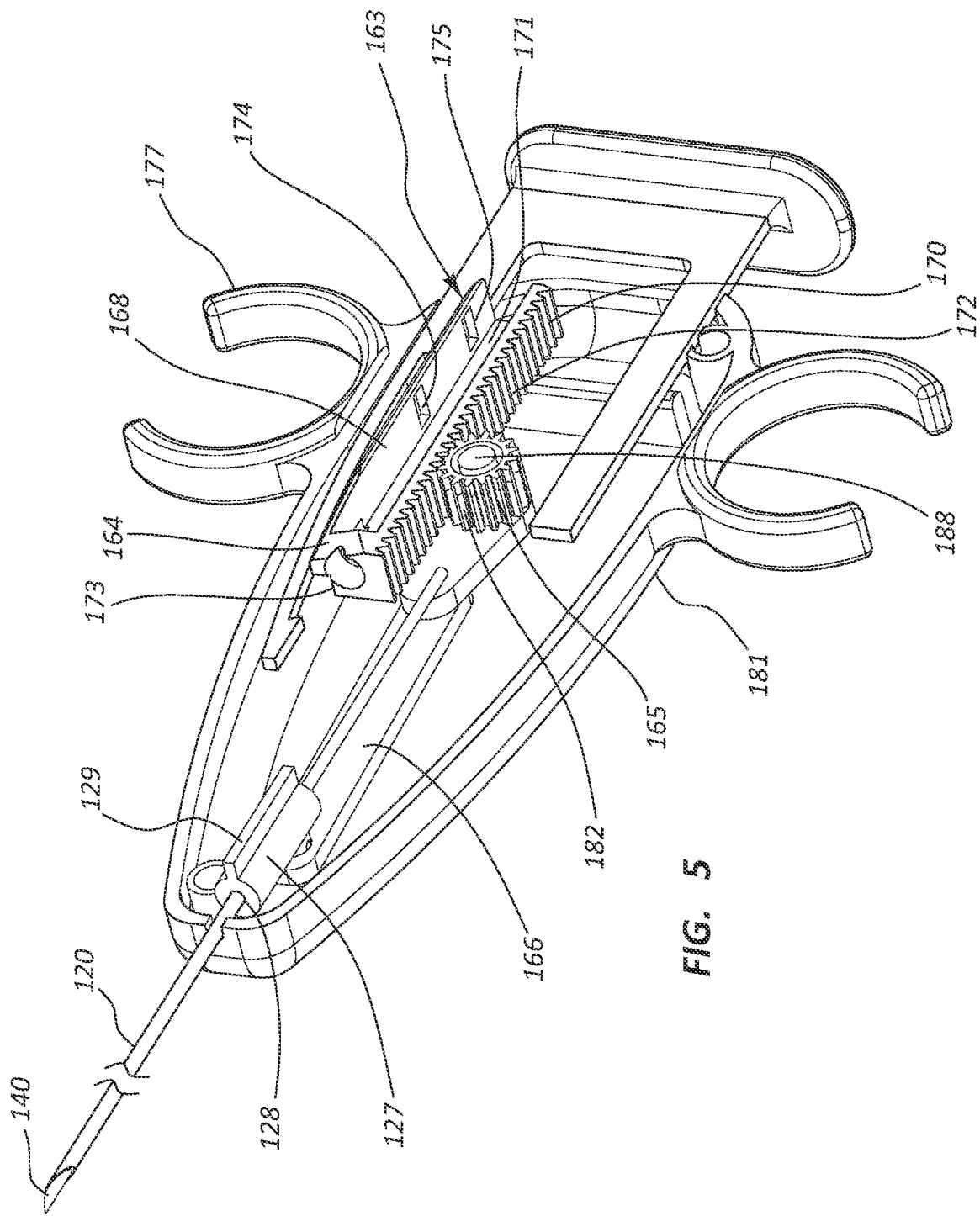
FIG. 5 is a perspective view of an actuator of the biopsy needle device of FIG. 1, shown with the housing base removed.

The cannula 120 and trocar 140 are configured such that when the biopsy needle device 100 is activated, the cannula 120 has motion relative to the trocar 140 exposing the notch 157 for tissue to prolapse into and returning to the initial position, thereby cutting or severing the tissue in the notch 157. Referring to FIGS. 4 and 5, in some embodiments the actuator 160 may comprise a housing base 180, the housing lid 181, a trigger 161, the cannula hub 121, a spring 162 and a linear displacement mechanism 163. The housing base 180 and the housing lid 181 may be configured to be coupled together utilizing various techniques, such as, snap fit, bonding, welding, etc., to enclose the components of the actuator 160. The actuator 160 may be configured to be held in the hand of a practitioner such that the biopsy needle device 100 may be manipulated during a medical procedure such as the Core Needle Biopsy procedure. The external surface of the housing base 180 and the housing lid 181 may comprise grip-enhancing features such as finger grips 177, bumps, dimples, grooves, ribs, other textures, overmolded soft material, etc. The housing base 180 and the housing lid 181 may be formed from a rigid plastic material and may be opaque or translucent.

In certain embodiments the linear displacement mechanism 163 may comprise a linear gear 164, a circular gear 165 and a linkage member 166. The linear gear 164 may comprise a side wall 168, a gear wall 170 and a cavity 171. The gear wall 170 may comprise gear teeth 172 configured to engage gear teeth 182 of the circular gear 165. The gear teeth 172 spacing and circular gear 165 diameter may be configured to adjust the force and speed of the movement of the mechanism 163. The gear teeth 172 of the linear gear 164 may be spaced along a longitudinal axis of the linear gear 164 from a distal end to a proximal end of the gear wall 170. The side wall 168 of the linear gear 164 may comprise a distal slot 173, a middle slot 174 and a proximal slot 175. The distal slot 173 may be configured to be engaged by the trigger 161 to move the linear gear 164 from a distal location to a proximal location when cocking the actuator 160. The middle slot 174 may be configured to engage a locking hook 153 of the housing base 180 when the linear gear 164 is in the proximal position and the actuator 160 cocked. The proximal slot 175 may be configured to engage the locking hook 153 when the linear gear 164 is in the distal position. The cavity 171 may be open at a proximal end and closed at a distal end. The spring (not shown) may be partially disposed within the cavity 171.

The circular gear 165 may comprise the gear teeth 182 and a torque converter 183. The circular gear 165 may be circular in shape with the gear teeth 182 spaced around a periphery. The gear teeth 182 may be configured to engage the gear teeth 172 of the linear gear 164 such that linear displacement of the linear gear 164 may be translated into rotational motion of the circular gear 165. For example, the linear gear 164 may be displaced by the force of the spring 162 from a proximal position to a distal position following activation of the actuator 160. The linear displacement of the linear gear 164 may result in rotational movement of the circular gear 165 when the gear teeth 172 of the linear gear 164 engage the gear teeth 182 of the circular gear 165. The circular gear 165 may be positioned within a circular pocket 184 comprising a wall 186. The circular pocket 184 may be partially open such that a portion of the wall 186 of the circular pocket 184 may be removed. Such an opening 185 in the circular pocket 184 may be configured to permit the engagement of the linear gear teeth 172 with the circular gear teeth 182.

In some embodiments, the torque converter 183 may be generally wedge shaped and comprise a circular passage 189 within the wide portion of the torque converter 183 and a mushroom shaped stud 190 near the narrow end of the torque converter 183. The torque converter 183 may be fixedly coupled to the circular gear 165. The coupling may be accomplished utilizing a pin 187 frictionally positioned within a bore 188 of the circular gear 165 and the circular passage 189 of the torque converter 183. Alternatively, the torque converter 183 and the circular gear 165 may be coupled utilizing any suitable technique, such as bonding, welding, etc. The distance between the center of the passage 189 and the center of the stud 190 may be approximately equivalent to one-half the length of the notch 157. For example, upon activation of the actuator 160, the distal end of the cannula 120 may move from a position distal to the notch 157 to a position proximal to the notch 157 and back to a position distal to the notch 157 as the torque converter 183 may rotate 360 degrees. The desired distance of proximal and distal movement of the distal end of the cannula 120 may be approximately the length of the notch 157. The torque converter 183 may rotate 180 degrees to move the distal end of the cannula 120 the desired proximal distance. The length of the torque converter 183 may be adjusted to accommodate different cannula 120 travel distances.

The torque converter 183 may be rotatably coupled to the linkage member 166. The linkage member 166 may comprise a proximal circular passage 191 and a distal circular passage 192. The proximal passage 191 may be configured to couple with the stud 190 of the torque converter 183 such that the linkage member 166 is permitted to rotate around the stud 190. The stud 190 may be split longitudinally such that the diameter of the stud 190 may decrease to permit passage of the mushroom shaped top of the stud 190 to pass through the proximal passage 191. The distal passage 192 may be configured to rotatably couple with a mushroom shaped stud (or snap) 126 of the cannula hub 121.

In some embodiments, the cannula hub 121 may comprise a body 127, a bore 128, the stud 126 and a rail 129. The stud 126 may project radially outward from the body 127 and be configured with a mushroom shaped end. The stud 126 may be split longitudinally such that the diameter of the stud 126 may decrease as the mushroom shaped end passes through the passage 192 of the linkage member 166. The rail 129 may extend radially outward from the body 127 opposite from the stud 126. The rail 129 may be slidingly coupled to guide rails 176 of the housing base 180. The bore 128 may be configured for positioning and coupling of the proximal end of the cannula 120 such that the trocar 140 may be disposed within the lumen 124 of the cannula 120.

The coupling of the cannula hub 121 to the torque converter 183 may translate the rotational movement of the torque converter 183 into linear movement of the cannula hub 121 and cannula 120. For example, the torque converter 183 may rotate 180 degrees in one direction as the actuator 160 may be cocked. As the torque converter 183 rotates 360 degrees, the linkage between the torque converter 183 and the cannula hub 121 may be configured to move the cannula hub 121 from a distal position to a proximal position and then back to the distal position. When the actuator 160 is activated, the torque converter 183 may rotate 360 degrees in an opposite direction resulting in the cannula hub 121 moving from the distal position to a proximal position and back to a distal position.

In certain embodiments, the trigger 161 comprises an activation flange 150, a cocking hook 151 and an activation hook 152. The trigger 161 may be partially disposed within the housing base 180. The activation flange 150 may be configured to permit the practitioner to grip the activation flange 150 and displace the trigger 161 proximally to cock the actuator 160. The activation flange 150 may also be configured to permit the practitioner to displace the trigger 161 distally to activate the actuator 160. A proximal face of the activation flange 150 may comprise grip-enhancing features, such as ribs, bumps, dimples, etc. The cocking hook 151 may be configured to engage the distal slot 173 of the linear gear 164 such that the cocking hook 151 may engage the distal slot 173 when the trigger 161 is displaced proximally, and the cocking hook 151 may disengage the distal slot 173 when the trigger 161 is displaced distally. The activation hook 152 may engage a post 154 coupled to the locking hook 153 of the housing base 180. The locking hook 153 may engage the middle slot 174 of the linear gear 164 such that the linear gear 164 may be locked in a cocked or proximal position. Distal displacement of the trigger 161 may result in engagement of the activation hook 152 with the post 154 such that the activation hook 152 may displace the post 154 and the locking hook 153 away from the linear gear 164. The locking hook 153 may be disengaged from the middle slot 174, and the linear gear 164 may be displaced distally.

In some embodiments, an introducer cannula (not shown) may be used with the biopsy needle device 100 disclosed herein. The introducer cannula may comprise an outer cannula sized to permit passage of the biopsy needle, a trocar slidingly positioned within the cannula and extending beyond the distal end of the cannula, and a depth stop to facilitate positioning of the introducer at the desired insertion depth. In use with the biopsy needle device 100, the introducer cannula assembly may be inserted into a patient's tissue, with the distal end of the introducer cannula positioned adjacent to the targeted tissue. The depth stop may be used to restrict insertion depth to a predetermined depth. The trocar may be removed. A portion of the biopsy needle device 100 may be inserted through the introducer cannula and into the targeted tissue. A tissue sample may be severed from the targeted tissue and retained within the biopsy needle device 100. The biopsy needle device 100 may be withdrawn from the targeted tissue and the introducer cannula. The tissue sample may be extracted from the biopsy needle device 100. If additional tissue samples are desired from the same target tissue, the process may be repeated. The introducer cannula is removed from the patient when all desired tissue samples have been collected.

Figure 7A:
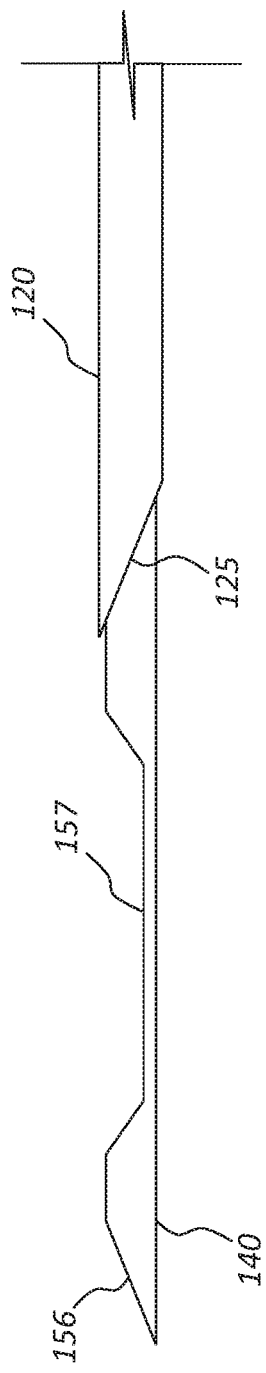
FIG. 7A is a schematic representation of portions of the cannula and trocar of the biopsy needle device of FIG. 1 in the second configuration correlating to FIG. 7.
Figure 7:
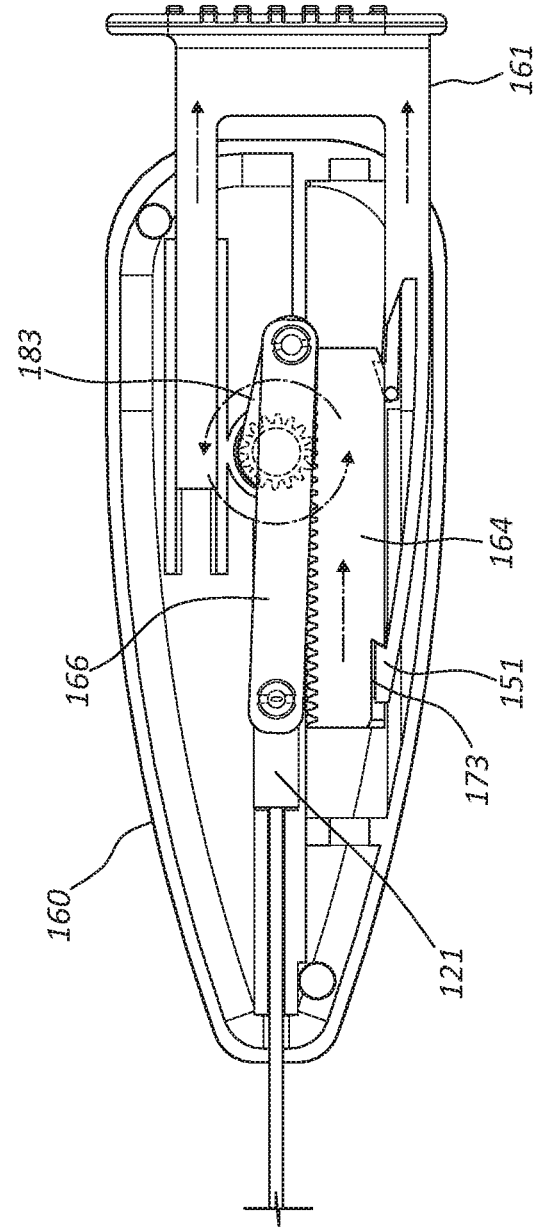
FIG. 7 is a schematic representation of portions of the biopsy needle device actuator of FIG. 1 in a second configuration.
Figure 9A:
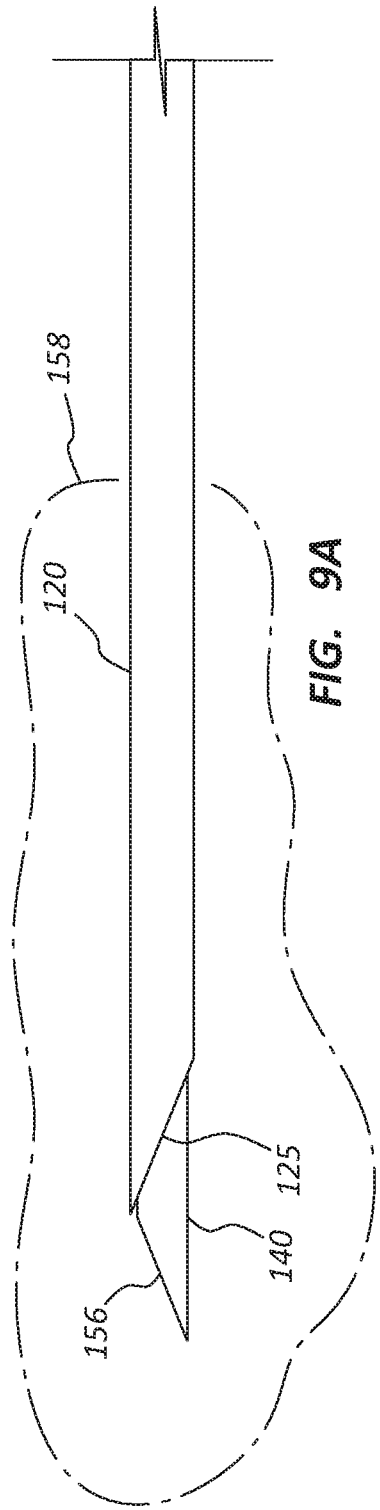
FIG. 9A is a schematic representation of portions of the cannula and trocar of the biopsy needle device of FIG. 1 in the fourth configuration correlating to FIG. 9.
Figure 9:
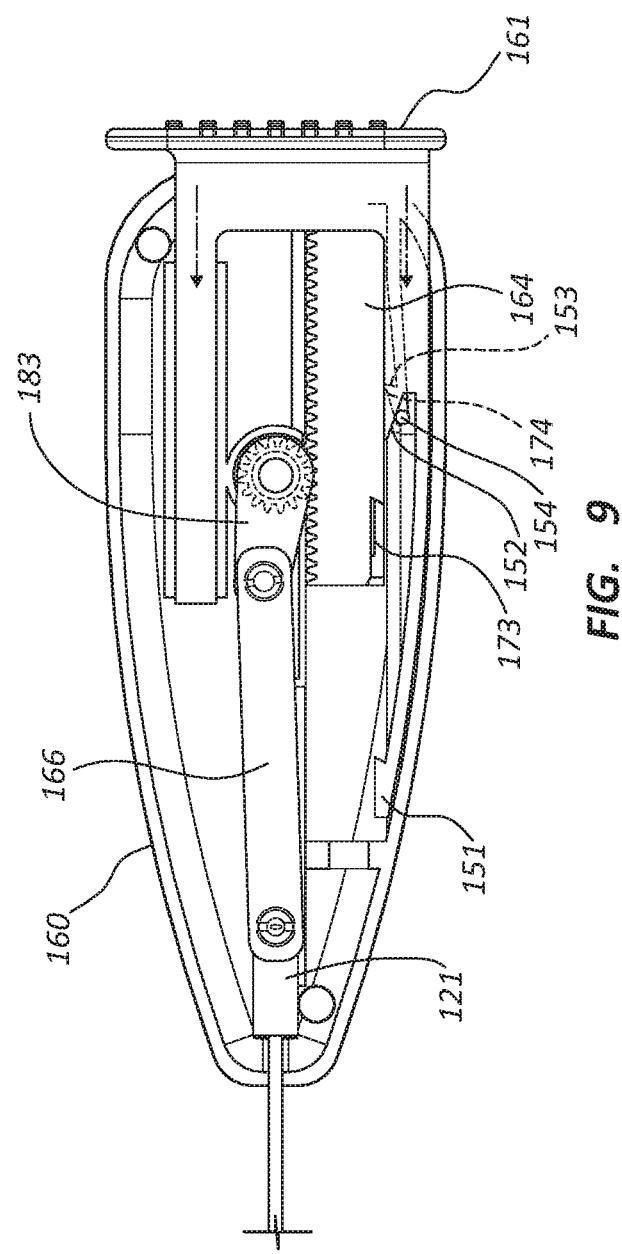
FIG. 9 is a schematic representation of portions of the biopsy needle device actuator of FIG. 1 in a fourth configuration.
Figure 10A:
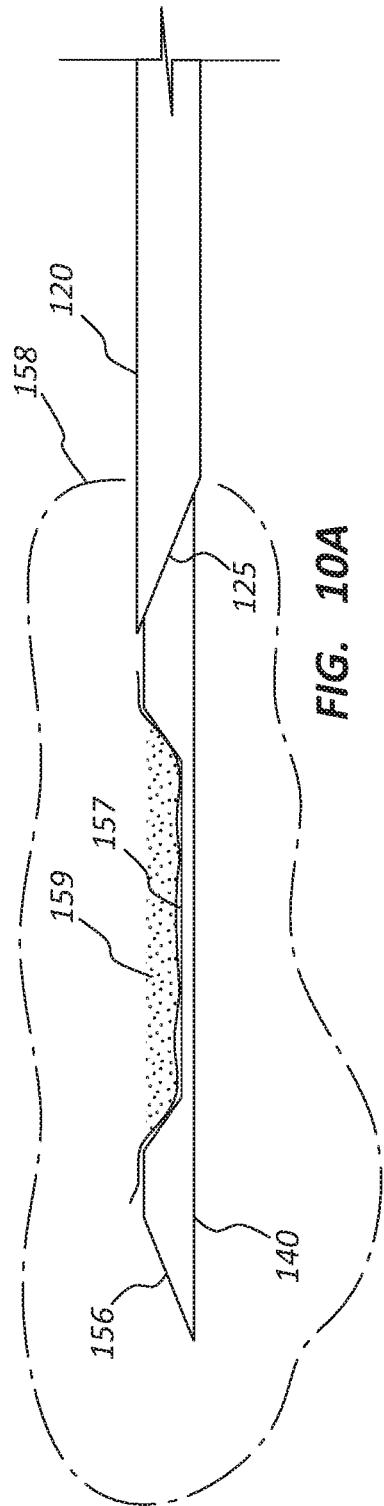
FIG. 10A is a schematic representation of portions of the cannula and trocar of the biopsy needle device of FIG. 1 in the fifth configuration correlating to FIG. 10.
Figure 10:
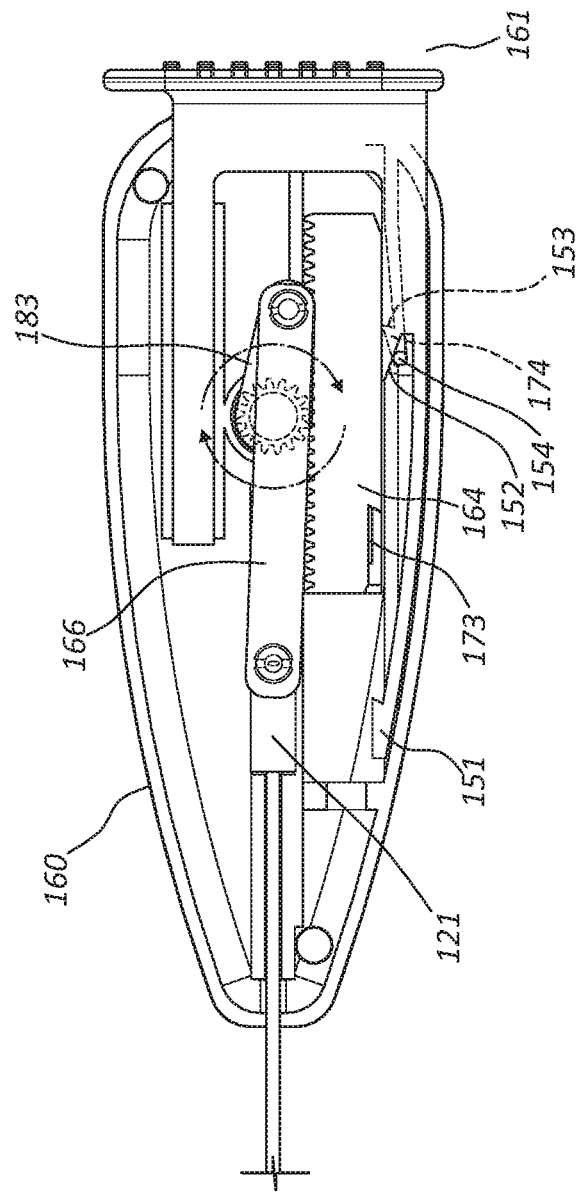
FIG. 10 is a schematic representation of portions of the biopsy needle device actuator of FIG. 1 in a fifth configuration.
Figure 11A:
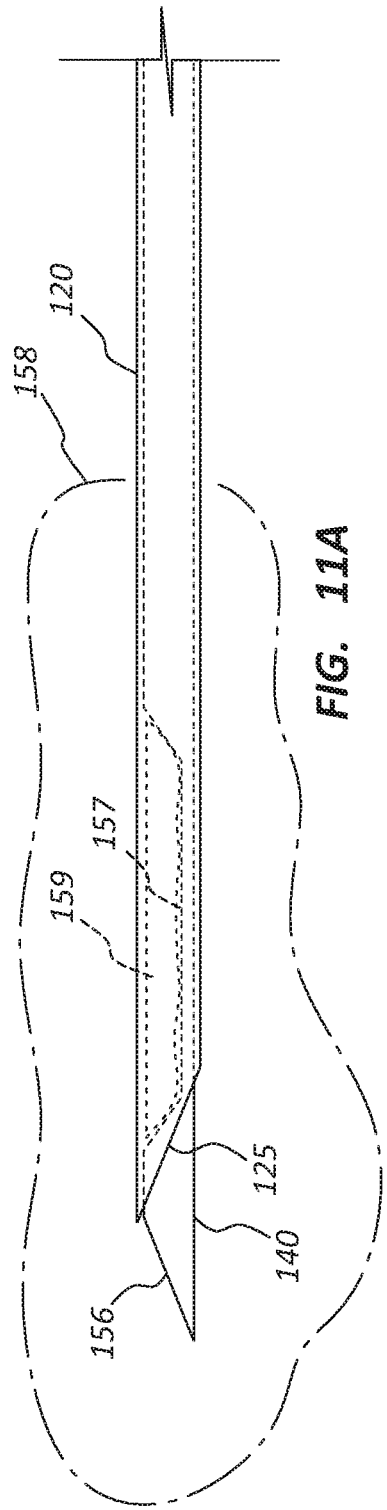
FIG. 11A is a schematic representation of portions of the cannula and trocar of the biopsy needle device of FIG. 1 in the sixth configuration correlating to FIG. 11.
Figure 11:
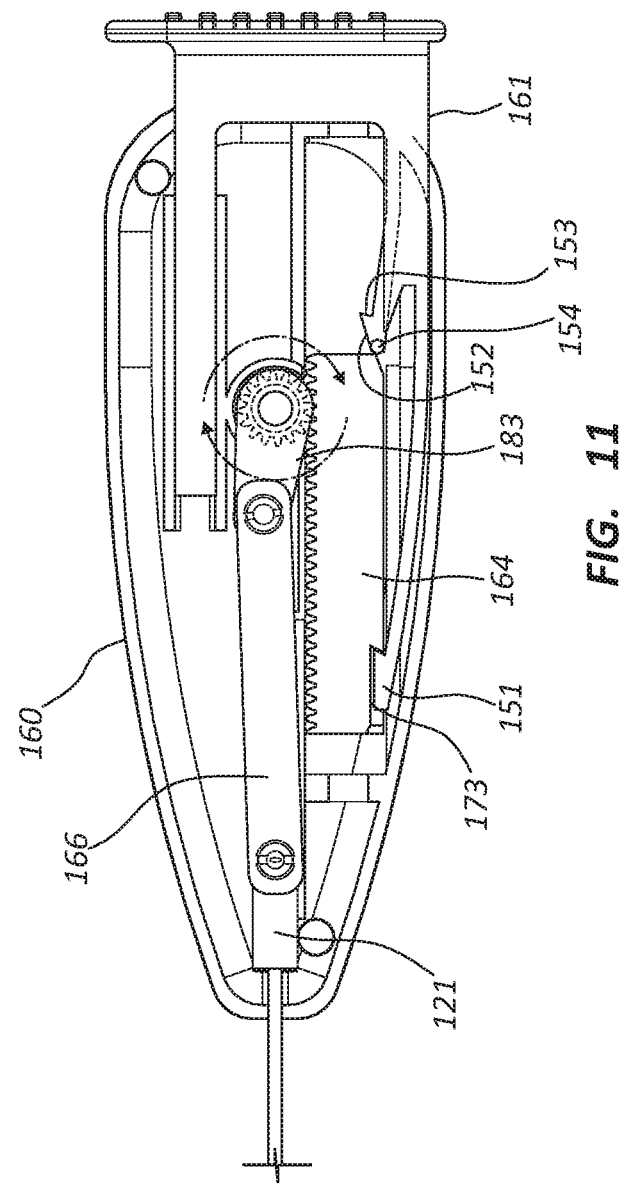
FIG. 11 is a schematic representation of portions of the biopsy needle device actuator of FIG. 1 in a sixth configuration.
Figure 12:
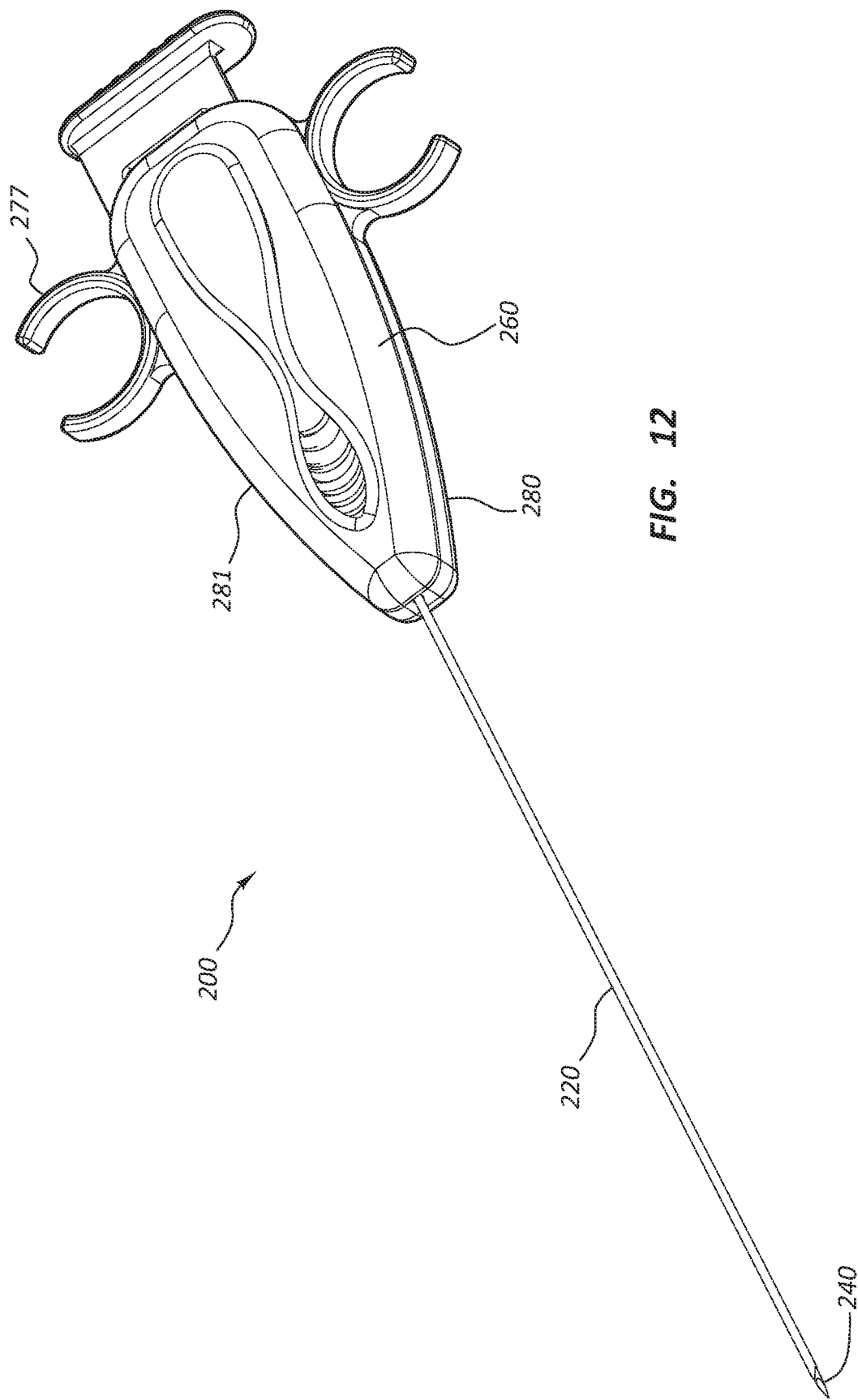
FIG. 12 is a perspective view of a second embodiment of the biopsy needle device.
Figure 13:
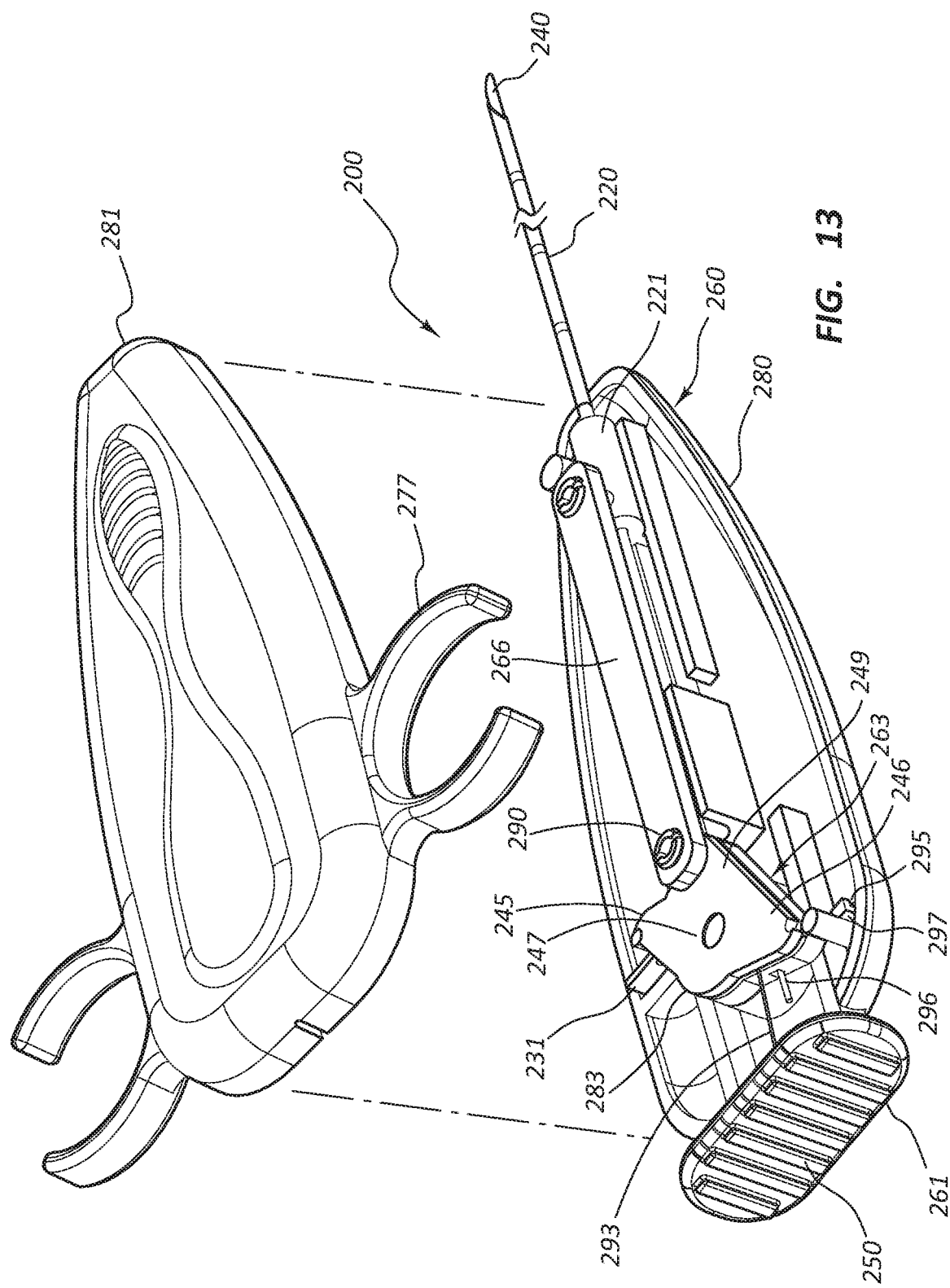
FIG. 13 is a perspective view of an actuator of the biopsy needle device of FIG. 12, shown with a housing lid removed.
Figure 14:
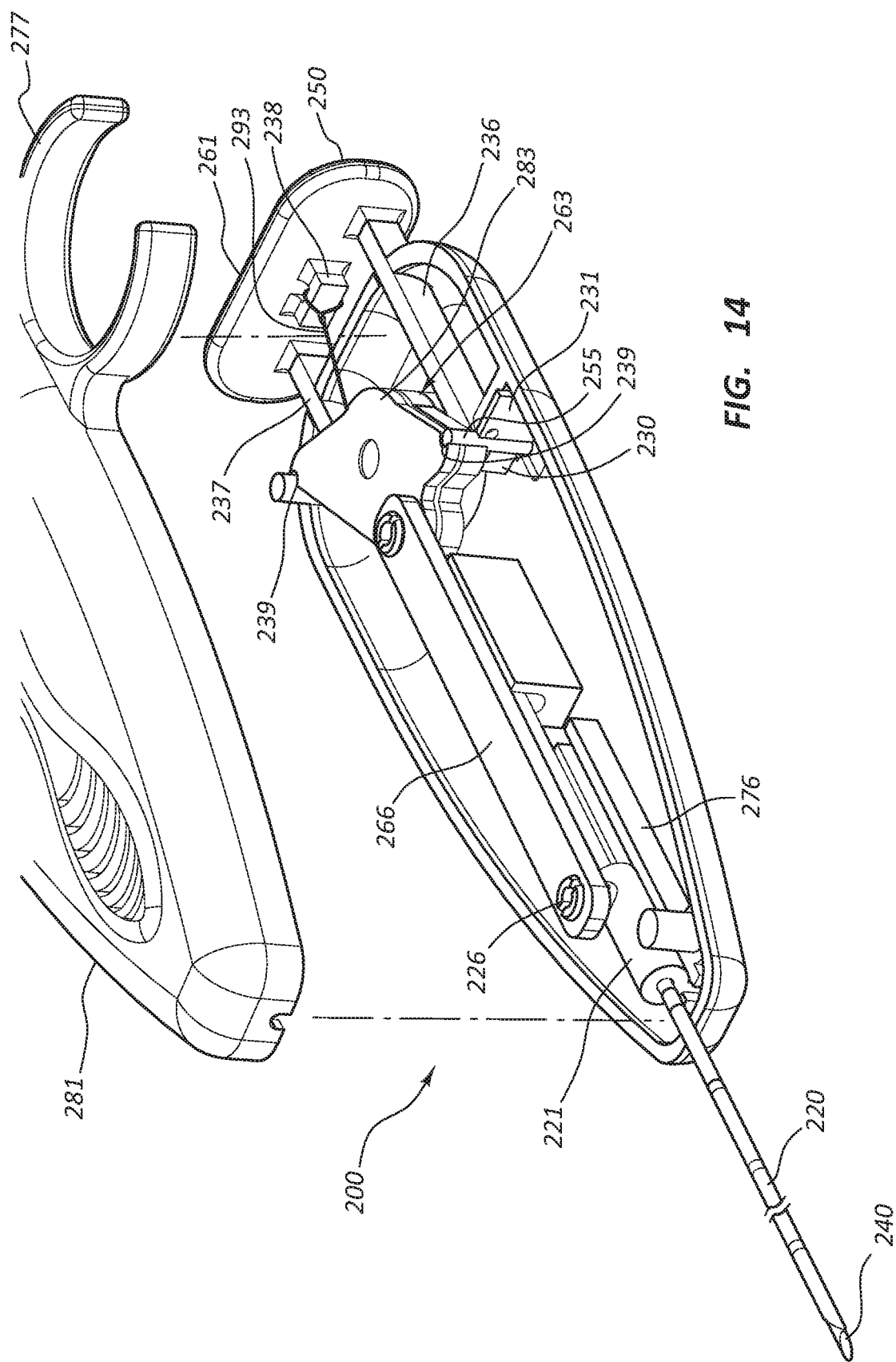
FIG. 14 is another perspective view of the actuator of the biopsy needle device of FIG. 12, shown with the housing lid removed.
Figure 15:
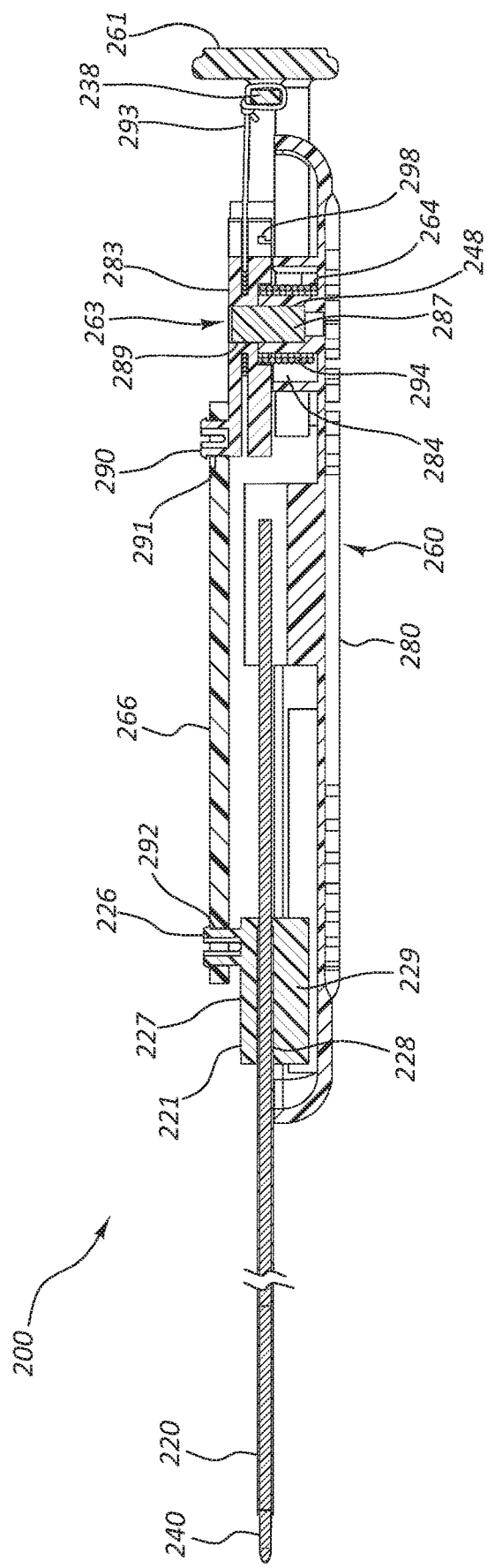
FIG. 15 is a cross-sectional view of the actuator of the biopsy needle device of FIG. 12 with the housing lid removed.

FIGS. 6-11A are schematic in nature. In other words, the figures show the functional and operational relationships of portions of the biopsy needle device 100 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cutaways of the tissues and/or organs. For example, a body tissue may be schematically shown with the biopsy needle device 100 disposed therein without indicating a cross-section portion or cutaway of a portion of the body tissue. FIGS. 6 and 6A are schematic representations of a side view of portions of the biopsy needle device 100 of FIG. 1 in a first configuration. FIG. 6A represents the relative positions of distal portions of the needle and cannula correlated with the actuator configuration of FIG. 6. FIGS. 7 and 7A are schematic representations of a side view of portions of the biopsy needle device 100 of FIG. 1 in a second configuration. FIG. 7A represents the relative positions of distal portions of the needle and cannula correlated with the actuator configuration of FIG. 7. FIGS. 8 and 8A are schematic representations of a side view of portions of the biopsy needle device 100 of FIG. 1 in a third configuration. FIG. 8A represents the relative positions of distal portions of the needle and cannula correlated with the actuator configuration of FIG. 8. FIGS. 9 and 9A are schematic representations of a side view of portions of the biopsy needle device 100 of FIG. 1 in a fourth configuration. FIG. 9A represents the relative positions of distal portions of the needle and cannula correlated with the actuator configuration of FIG. 9. FIGS. 10 and 10A are schematic representations of a side view of portions of the biopsy needle device 100 of FIG. 1 in a fifth configuration. FIG. 10A represents the relative positions of distal portions of the needle and cannula correlated with the actuator configuration of FIG. 10. FIGS. 11 and 11A are schematic representations of a side view of portions of the biopsy needle device 100 of FIG. 1 in a sixth configuration. FIG. 11A represents the relative positions of distal portions of the needle and cannula correlated with the actuator configuration of FIG. 11.

FIG. 6 illustrates the relative locations of the linear gear 164, the torque converter 183, the cannula hub 121 and the trigger 161 within the actuator 160 in the first configuration. The first configuration may be prior to cocking of the actuator 160 by the practitioner. As can be seen, the cannula hub 121 may be positioned at the distal end portion of the housing base 180. The linear gear 164 may be positioned at a distal position. The torque converter 183 may be oriented such that the narrow portion may be directed distally. The trigger 161 may be positioned in a distal position such that the cocking hook 151 engages the distal slot 173 of the linear gear 164.

FIG. 6A illustrates distal portions of the cannula 120 and the trocar 140 of the needle device 100 in the first configuration. As can be seen, the trocar bevel 156 may extend beyond the distal end of the cannula 120. The cannula bevel 125 may be located proximal to and adjacent to the trocar bevel 156.

FIG. 7 illustrates the relative locations of the linear gear 164, the torque converter 183, the cannula hub 121 and the trigger 161 within the actuator 160 in the second configuration. The second configuration may be approximately halfway through cocking of the actuator 160 by the practitioner. An intermediate latch (not shown) may be configured into the linear gear 164 as to be able to hold this position. As can be seen, the cannula hub 121 may be displaced proximally and may be positioned at a proximal position. The linear gear 164 may be displaced proximally and positioned at an intermediate position. The torque converter 183 may be rotated in the direction of the arrow and oriented such that the narrow portion may be directed proximally. The trigger 161 may be displaced proximally and may be positioned in an intermediate position. Following collection of a tissue sample 159, the actuator 160 may be reset to the second configuration to retrieve the tissue sample 159 from the notch 157.

FIG. 7A illustrates distal portions of the cannula 120 and the trocar 140 of the needle device 100 in the second configuration. The cannula bevel 125 may be displaced proximally and may be positioned proximal to the notch 157 such that the cannula 120 does not cover the notch 157.

FIG. 8 illustrates the relative locations of the linear gear 164, the torque converter 183, the cannula hub 121 and the trigger 161 within the actuator 160 in the third configuration. The third configuration may be subsequent to cocking of the actuator 160 and insertion of the trocar 140 and cannula 120 into the lesion 158 by the practitioner. As can be seen, the cannula hub 121 may be displaced distally and may be positioned at the distal end portion of the housing base 180. The linear gear 164 may be further displaced proximally and may be positioned at a proximal position. The torque converter 183 may be further rotated in the direction of the arrow and may be oriented such that the narrow portion may be directed distally. The trigger 161 may be further displaced proximally and may be positioned in a proximal position.

FIG. 8A illustrates distal portions of the cannula 120 and the trocar 140 of the needle device 100 in the third configuration. As can be seen, the trocar bevel 156 may extend beyond the cannula bevel 125 and the notch 157 may be covered by the cannula 120. The distal end of the cannula 120 may be displaced distally and may be positioned proximal to and adjacent to the trocar bevel 156.

FIG. 9 illustrates the relative locations of the linear gear 164, the torque converter 183, the cannula hub 121 and the trigger 161 within the actuator 160 in the fourth configuration. The fourth configuration may occur as the actuator 160 is activated by the practitioner. As can be seen, the cannula hub 121 may be positioned at the distal end portion of the housing base 180. The linear gear 164 may be positioned at a proximal position. The torque converter 183 may be oriented such that the narrow portion may be directed distally. The trigger 161 may be displaced distally and may be positioned in an intermediate position such that the activation hook 152 may displace the post 154, and the locking hook 153 may disengage from the slot 174 of the linear gear 164.

FIG. 9A illustrates distal portions of the cannula 120 and the trocar 140 of the needle device 100 in the fourth configuration. As can be seen, the trocar bevel 156 may extend beyond the distal end of the cannula 120. The cannula bevel 125 may be located proximal to and adjacent to the trocar bevel 156.

FIG. 10 illustrates the relative locations of the linear gear 164, the torque converter 183, the cannula hub 121 and the trigger 161 within the actuator 160 in the fifth configuration. The fifth configuration may be approximately halfway through activation of the actuator 160. As can be seen, the cannula hub 121 may be displaced proximally and may be positioned at a proximal position. The linear gear 164 may be displaced distally and may be positioned at an intermediate position. The torque converter 183 may be rotated in the direction of the arrow and may be oriented such that the narrow portion may be directed proximally. It is to be understood that the rotation of the torque converter 183 is a continuous motion for approximately 360 degrees. That is, the rotational motion of the torque converter 183 does not stop after rotating 180 degrees. Rather, the torque converter 183 has continuous rotational movement for approximately 360 degrees. The fifth configuration represents an instant of time as the torque converter 183 continuously rotates. The trigger 161 may be positioned in an intermediate position.

FIG. 10A illustrates distal portions of the cannula 120 and the trocar 140 of the needle device 100 in the fifth configuration. The cannula bevel 125 may be displaced proximally and may be positioned proximal to the notch 157 such that the cannula 120 does not cover the notch 157. The tissue sample 159 may collapse or prolapse into the notch 157 and may at least partially fill the notch 157.

FIG. 11 illustrates the relative locations of the linear gear 164, the torque converter 183, the cannula hub 121 and the trigger 161 within the actuator 160 in the sixth configuration. The sixth configuration may be subsequent to activation of the actuator 160 and severing of the tissue sample 159. As can be seen, the cannula hub 121 may be displaced distally and may be positioned at a distal position. The linear gear 164 may be displaced distally and may be positioned at a distal position. The torque converter 183 may be rotated in the direction of the arrow and may be oriented such that the narrow portion may be directed distally. The trigger 161 may be positioned in a distal position.

FIG. 11A illustrates distal portions of the cannula 120 and the trocar 140 of the needle device 100 in the sixth configuration. As can be seen, the trocar bevel 156 may extend beyond the distal end of the cannula 120. The cannula bevel 125 may be displaced distally such that the bevel 125 may cut or sever the tissue sample 159 from the lesion 158, and the cannula 120 may cover the notch 157 such that the tissue sample 159 may be retained in the notch 157. The distal end of the cannula 120 may be positioned proximal to and adjacent to the trocar bevel 156.

In some embodiments, the biopsy needle device 100 may permit the practitioner to perform the Core Needle Biopsy procedure. The location of the tissue or lesion to be biopsied within the patient may be identified utilizing known diagnosis techniques such as computed tomography, magnetic resonance imaging, x-ray, fluoroscopy, ultrasound, etc. The patient may be positioned and prepped for the Core Needle Biopsy procedure. The practitioner may obtain the sterilized biopsy needle device 100 configured with the desired trocar and cannula length and diameter and the desired length of notch 157 such that a desired sample length may be collected. The practitioner may prep the biopsy needle device 100 by cocking the actuator 160. The actuator 160 may be cocked by displacing the activation flange 150 proximally. The cocking hook 151 may engage the distal slot 173 of the linear gear 164 displacing the linear gear 164 proximally until the locking hook 153 engages the middle slot 174, and the spring 162 may be at least partially compressed. The practitioner may insert the cannula 120 and the trocar 140 through the skin and into the lesion of the patient while holding the actuator 160 in a hand. Alternatively, the cannula 120 and the trocar 140 may be inserted into the lesion of a patient utilizing an introducer cannula that was previously inserted into the patient. The practitioner may confirm the position of the distal end portions 122, 142 of the cannula 120 and trocar 140 utilizing known techniques such as ultrasound, fluoroscopy, computed tomography, etc. The practitioner may activate the actuator 160 by applying a force to the activation flange 150 resulting in the activation hook 152 engaging the post 154 and disengaging the locking hook 153 from the middle slot 174 of the linear gear 164. The spring 162 may decompress and the linear gear 164 may be displaced distally. The gear teeth 172 of the linear gear 164 may engage the gear teeth 182 of the circular gear 165, causing the circular gear 165 to rotate. The torque converter 183 coupled to the circular gear 165 may rotate approximately 360 degrees in a continuous motion. The rotational movement of the torque converter 183 may be translated into an initial proximal and then distal linear movement of the cannula hub 121 and cannula 120 through the linkage member 166. The torque converter 183 may rotate 180 degrees and the cannula hub 121 and cannula 120 may be displaced proximally to a maximum proximal position. The distal end of the cannula 120 may be located proximally of the notch 157 of the trocar 140. The notch 157 may be exposed to lesion tissue. A portion of the lesion tissue may collapse into the notch 157. The torque converter 183 may complete the 360 degree rotation, and the cannula hub 121 and the cannula 120 may be displaced to a distal position. The distal end of the cannula 120 may slide over the notch 157 and cut or sever the portion of the lesion or tissue sample 159 within the notch 157 from the surrounding lesion tissue.

The tissue sample 159 may be captured and retained within the notch 157 by the cannula 120. The cannula 120 and the trocar 140 may be removed from the patient's tissue. The tissue sample 159 may be extracted from the biopsy needle device 100 and analyzed using known techniques.

Referring to FIGS. 12-15, an embodiment of the actuator 260 of a biopsy needle device 200 is shown. Like numbers for like components of the biopsy needle device 100 as described above will be utilized to describe the biopsy needle device 200. A trocar 240 and a cannula 220 are identical to the trocar 140 and the cannula 120 described above and illustrated in FIGS. 2-3A are thus not described in detail with the other components of the biopsy needle device 200, though disclosure relating to the structure, function, and other aspects of these components recited in connection with the biopsy needle device 100 may be analogously applied to the components of the biopsy needle device 200.

In some embodiments the actuator 260 may comprise a housing base 280, a housing lid 281, a trigger 261, a cannula hub 221, and a torsional spring mechanism 263. The housing base 280 and the housing lid 281 may be configured to be coupled together utilizing various techniques, such as pins and sockets, snap fit, bonding, welding, etc., to enclose the components of the actuator 260. The actuator 260 may be configured to be held in the hand of a practitioner such that the biopsy needle device 200 may be manipulated during a medical procedure such as the Core Needle Biopsy procedure. The external surface of the housing base 280 and the housing lid 281 may comprise grip-enhancing features such as finger grips 277, bumps, dimples, grooves, ribs, other textures, overmolded soft material, etc. The housing base 280 and the housing lid 281 may be formed from a rigid plastic material and may be opaque or translucent.

In certain embodiments the torsional spring mechanism 263 may comprise a torsional spring 264, a torque converter 283, a flexible member 293 and a linkage member 266. The torsional spring 264 may comprise a coil portion 294, a first end 295, and a second end 296. The coil portion 294 may be disposed within an annular pocket 284 of the base 280. The first end 295 may extend away from the annular pocket 284 and be coupled to the base 280 at an "L" shaped protrusion 297. The first end 295 is configured to remain in a fixed position relative to the base 280. The second end 296 may also extend away from the annular pocket 284 and be coupled to the torque converter 283 at a slot 298. The second end 296 is configured to rotate with the torque converter 283 such that the torsional spring 264 may be wound and unwound. The torsional spring 264 may be made from any suitable spring type material, such as brasses, bronzes, carbon steels, Inconel alloys, stainless steels, titanium alloys, etc.

In some embodiments, the torque converter 283 may comprise a first arm 245 and a second arm 246. The arms 245, 246 may extend from a central portion 247. The arms 245, 246 may be configured at 180° from one another. A "C" shaped catch 239 may be located at the end of arms 245, 246. The catch 239 may be configured to releasably couple with a post 255 of the base 280. The central portion 247 may comprise a bore 289 configured to fixedly couple with a pin 287. The pin 287 is configured to rotationally couple with a recess 248 at the core of the annular pocket 284. The torque converter 283 may further comprise a third arm 249 extending from the central portion 247 between the first arm 245 and the second arm 246. The third arm 249 may comprise a mushroom shaped stud 290 configured to couple with the linkage member 266.

The torque converter 283 may be rotatably coupled to the linkage member 266. The linkage member 266 may comprise a proximal circular passage 291 and a distal circular passage 292. The proximal passage 291 may be configured to couple with the stud 290 of the torque converter 283 such that the linkage member 266 is permitted to rotate around the stud 290. The stud 290 may be split longitudinally such that the diameter of the stud 290 may decrease to permit passage of the mushroom shaped top of the stud 290 to pass through the proximal passage 291. The distal passage 292 may be configured to rotatably couple with a mushroom shaped stud 226 of the cannula hub 221.

In some embodiments, the cannula hub 221 may comprise a body 227, a bore 228, the stud 226 and a rail 229. The stud 226 may project radially outward from the body 227 and be configured with a mushroom shaped end. The stud 226 may be split longitudinally such that the diameter of the stud 226 may decrease as the mushroom shaped end passes through the distal passage 292 of the linkage member 266. The rail 229 may extend radially outward from the body 227 opposite from the stud 226. The rail 229 may be slidingly coupled to guide rails 276 of the housing base 280. The bore 228 may be configured for positioning and coupling of the proximal end of the cannula 220 such that the trocar 240 may be disposed within a lumen 224 of the cannula 220.

The coupling of the cannula hub 221 to the torque converter 283 is configured to translate the rotational movement of the torque converter 283 into linear movement of the cannula hub 221 and cannula 220. For example, the torque converter 283 may rotate 360 degrees in one direction as the actuator 260 is cocked. As the torque converter 283 rotates 360 degrees, the linkage between the torque converter 283 and the cannula hub 221 is configured to move the cannula hub 221 from a distal position to a proximal position and then back to the distal position. When the actuator 260 is activated, the torque converter 283 may rotate 360 degrees in an opposite direction resulting in the cannula hub 221 moving from the distal position to a proximal position and back to a distal position resulting in the cannula 220 moving proximally over the trocar 240 to expose a notch 257 to collect a tissue sample and then moving distally to cover the notch 257 and retain the tissue sample.

In certain embodiments, the trigger 261 comprises an activation flange 250, a first arm 236, and a second arm 237. The trigger 261 may extend proximally from the base 280 and the arms 236, 237 may be partially disposed within the base 180. The activation flange 250 may be configured to permit the practitioner to grip the activation flange 250 and displace the trigger 261 proximally to cock the actuator 260. The activation flange 250 may also be configured to permit the practitioner to displace the trigger 261 distally to activate the actuator 260. A proximal face of the activation flange 250 may comprise grip-enhancing features, such as ribs, bumps, dimples, etc. A distal face of the activation flange 250 may comprise a loop 238 configured to fixedly couple with the flexible member 293.

The first arm 236 may be configured to engage a flange 230 that extends from the post 255 of the base 280. A cantilever beam 231 may couple the post 255 to the base 280 such that the post 255 is movable distally and/or proximally. The post 255 is configured to be deflected when the first arm 236 moves distally and engages the flange 230. The post 255 is also configured to return to a non-deflected position when the first arm 236 no longer engages the flange 230 due to the elasticity of the material of the cantilever beam 231. The second arm 237 may be configured to guide the trigger 261 as it is moved proximally and distally.

In some embodiments, the flexible member 293 may be coupled to the torque converter 283 at one end and the trigger 261 at another end. The flexible member 293 may be coiled around a portion of the torque converter 283 such that when tension is applied to the flexible member 293 the flexible member uncoils, the torque converter 283 rotates, and the torsional spring 264 winds. When the tension is released and the actuator 260 is activated, the torsional spring 264 unwinds, causing the torque converter 283 to rotate in the opposite direction, and the flexible member 293 winds around a portion of the torque converter 283. The flexible member 293 may be fixedly coupled to the loop 238 of the trigger 261 such that when the trigger 261 is moved proximally to cock the actuator 260, tension is applied to the flexible member 293 resulting in rotation of the torque converter 283. The flexible member 293 may be coupled to the loop 238 utilizing techniques known in the art, such as tying, boding, welding, etc. The flexible member 293 may be formed from flexible materials such as braided threads, monofilament plastics, metals wires, etc.

Figure 18:
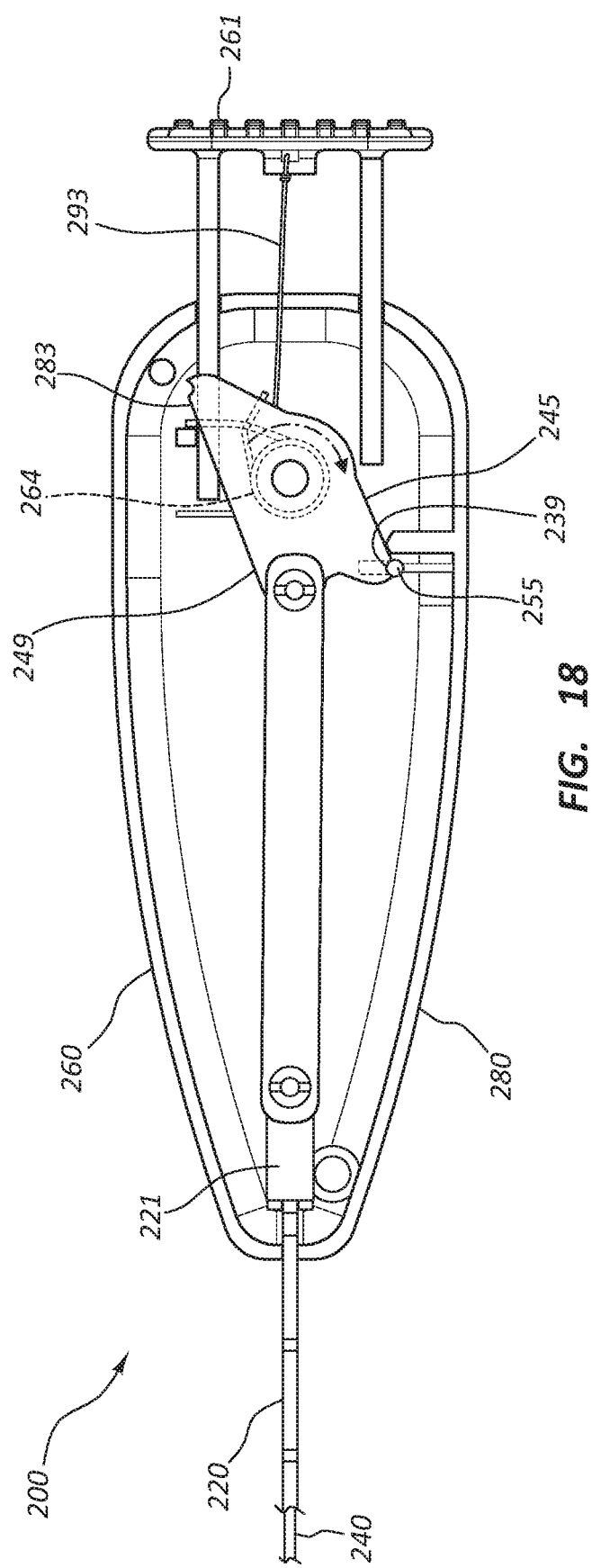
FIG. 18 is a schematic representation of portions of the biopsy needle device actuator of FIG. 12 in a third configuration.
Figure 18A:
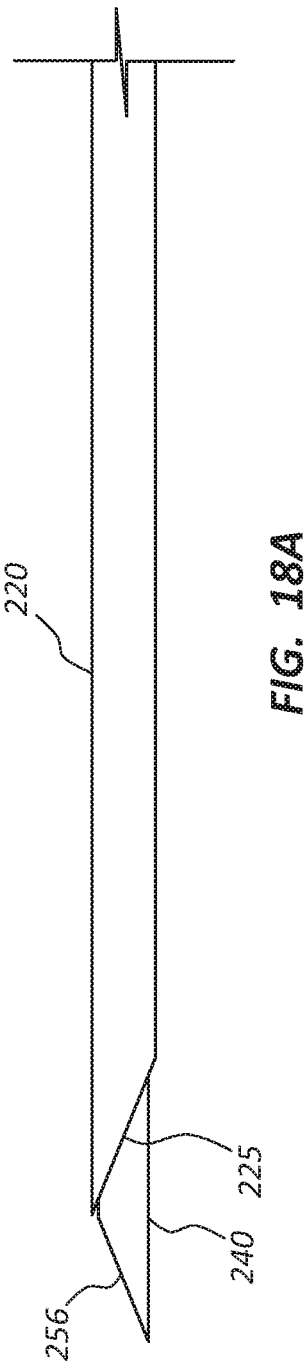
FIG. 18A is a schematic representation of portions of the cannula and trocar of the biopsy needle device of FIG. 12 in the third configuration correlating to FIG. 18.
Figure 19:
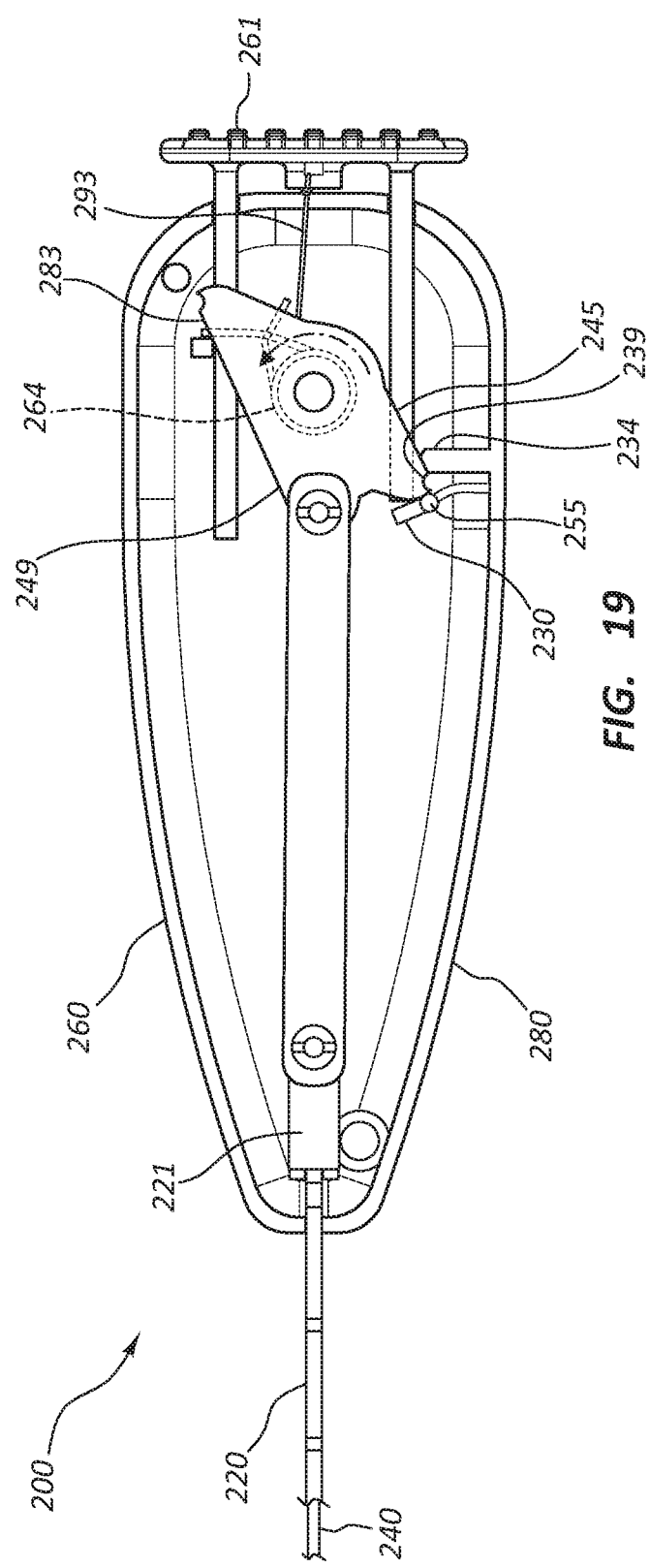
FIG. 19 is a schematic representation of portions of the biopsy needle device actuator of FIG. 12 in a fourth configuration.
Figure 19A:
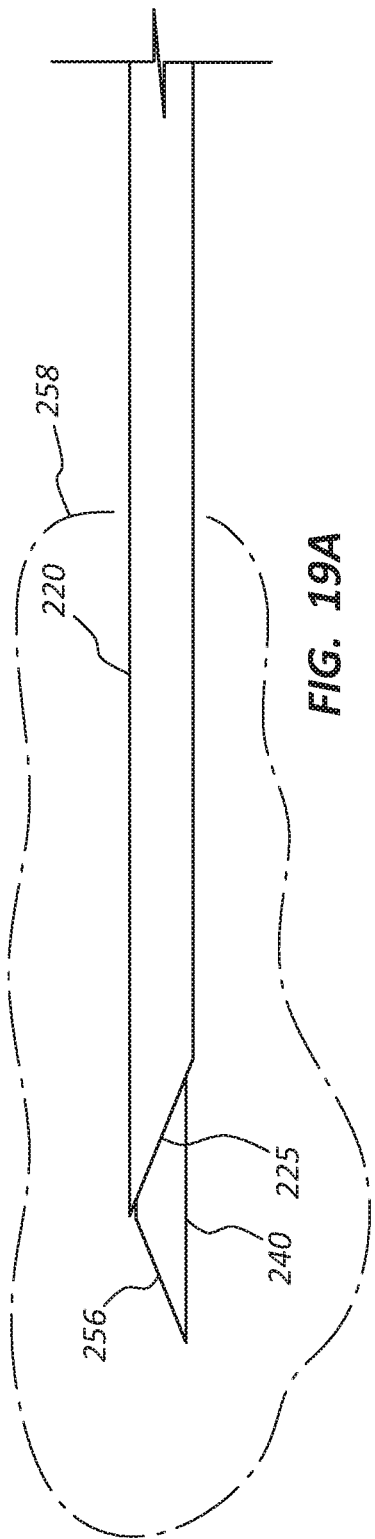
FIG. 19A is a schematic representation of portions of the cannula and trocar of the biopsy needle device of FIG. 12 in the fourth configuration correlating to FIG. 19.
Figure 21:
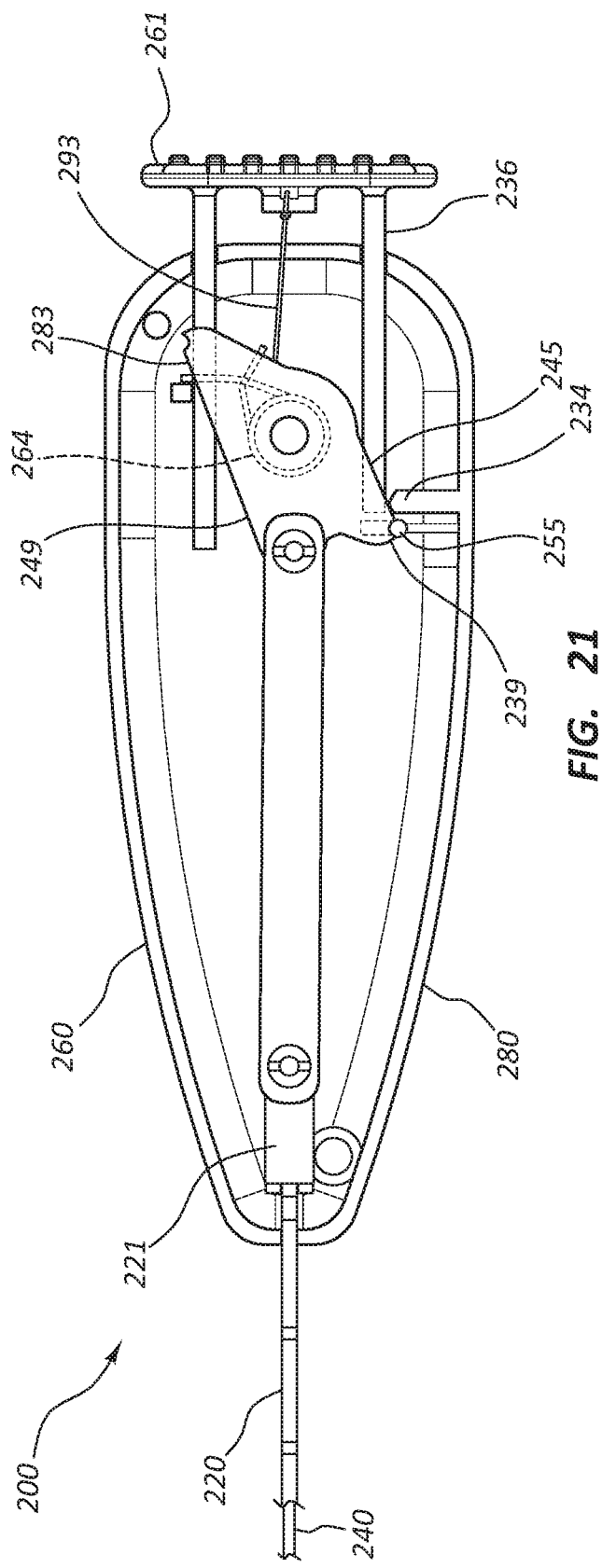
FIG. 21 is a schematic representation of portions of the biopsy needle device actuator of FIG. 12 in a sixth configuration.
Figure 21A:
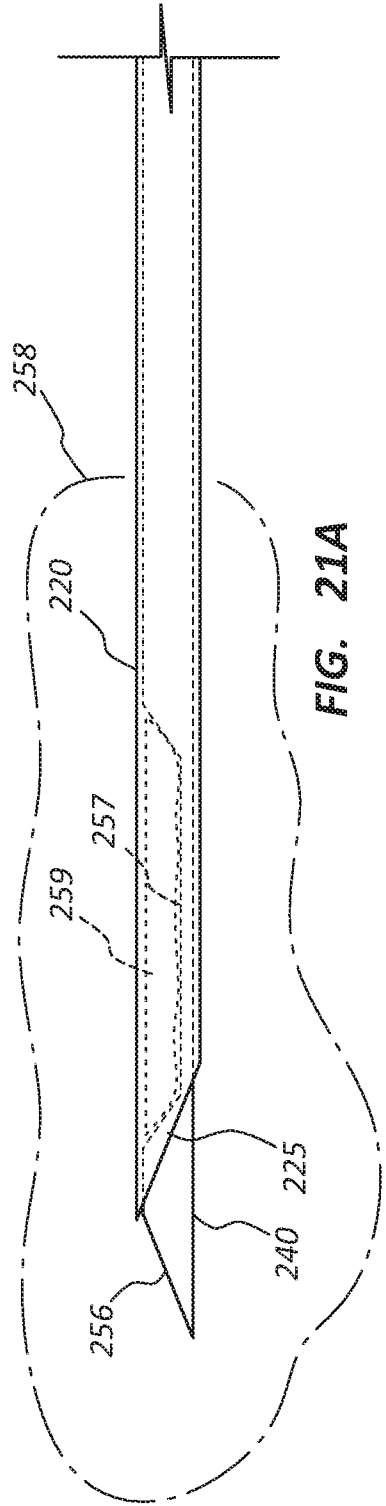
FIG. 21A is a schematic representation of portions of the cannula and trocar of the biopsy needle device of FIG. 12 in the sixth configuration correlating to FIG. 21.
Figure 22:
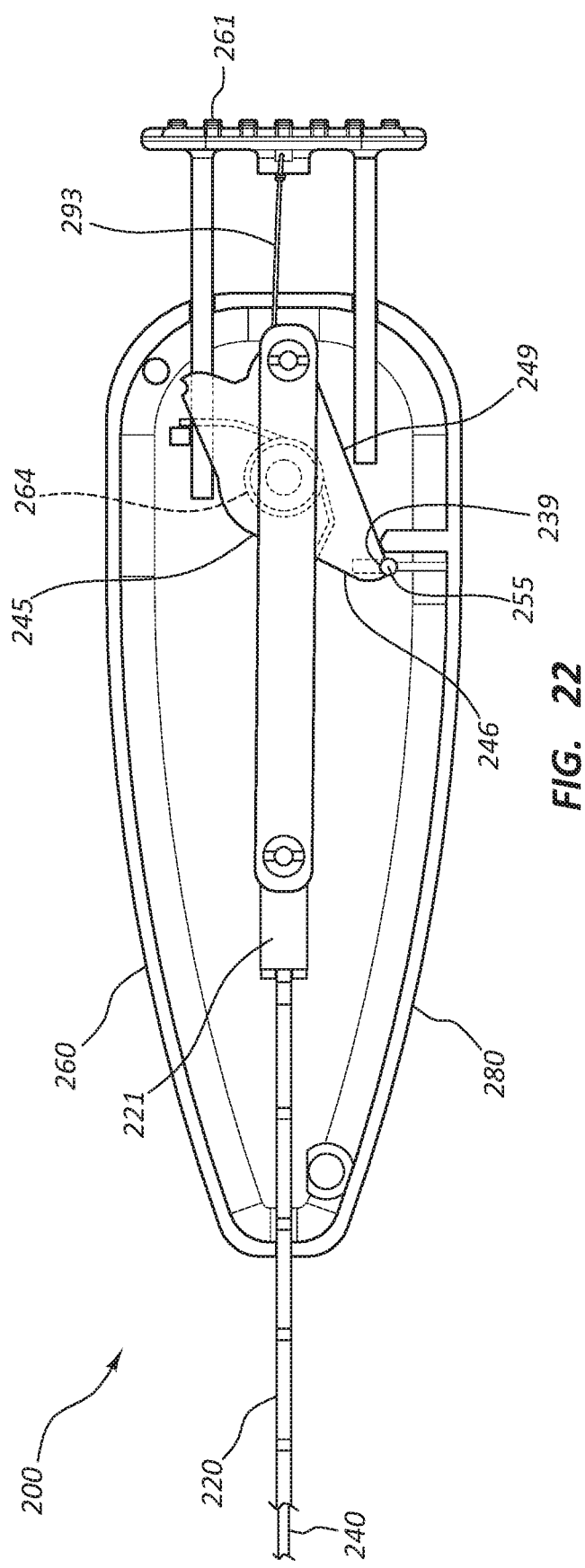
FIG. 22 is a schematic representation of portions of the biopsy needle device actuator of FIG. 12 in a seventh configuration.
Figure 22A:
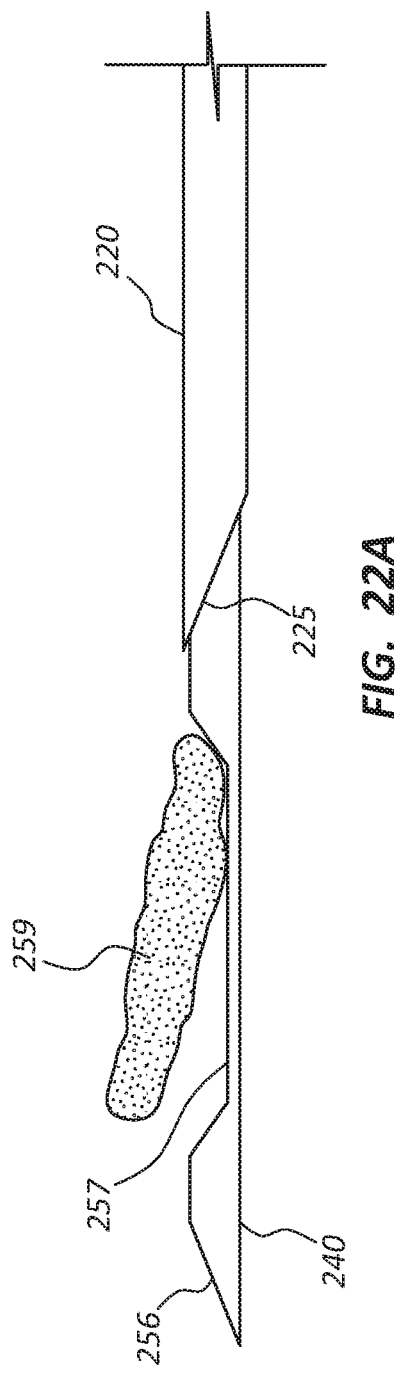
FIG. 22A is a schematic representation of portions of the cannula and trocar of the biopsy needle device of FIG. 12 in the seventh configuration correlating to FIG. 22.

FIGS. 16-22A are schematic in nature. In other words, the figures show the functional and operational relationships of portions of the biopsy needle device 200 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cutaways of the tissues and/or organs. For example, a body tissue may be schematically shown with the biopsy needle device 200 disposed therein without indicating a cross-section portion or cutaway of a portion of the body tissue. FIG. 16 is a schematic representation of a side view of portions of the actuator 260 of FIGS. 13-15 in a first configuration. FIG. 16A represents the relative positions of the distal portions of the trocar 240 and cannula 220 correlated with the actuator configuration of FIG. 16. FIG. 17 is a schematic representation of a side view of portions of the actuator 260 of FIGS. 13-15 in a second configuration. FIG. 17A represents the relative positions of the proximal portions of the trocar 240 and cannula 220 correlated with the actuator 260 configuration of FIG. 17. FIG. 18 is a schematic representation of a side view of portions of the actuator 260 of FIGS. 13-15 in a third configuration. FIG. 18A represents the relative positions of the distal portions of the trocar 240 and cannula 220 correlated with the actuator configuration of FIG. 18. FIG. 19 is a schematic representation of a side view of portions of the actuator 260 of FIGS. 13-15 in a fourth configuration. FIG. 19A represents the relative positions of the distal portions of the trocar 240 and cannula 220 correlated with the actuator configuration of FIG. 19. FIG. 20 is a schematic representation of a side view of portions of the actuator 260 of FIGS. 13-15 in a fifth configuration. FIG. 20A represents the relative positions of the distal portions of the trocar 240 and cannula 220 correlated with the actuator configuration of FIG. 20. FIG. 21 is a schematic representation of a side view of portions of the actuator 260 of FIGS. 13-15 in a sixth configuration. FIG. 21A represents the relative positions of the distal portions of the trocar 240 and cannula 220 correlated with the actuator configuration of FIG. 21. FIG. 22 is a schematic representation of a side view of portions of the actuator 260 of FIGS. 13-15 in a seventh configuration. FIG. 22A represents the relative positions of the distal portions of the trocar 240 and cannula 220 correlated with the actuator configuration of FIG. 22.

FIG. 16 illustrates the relative locations of the torsional spring 264, the torque converter 283, the cannula hub 221 and the trigger 261 within the actuator 260 in the first configuration. The first configuration may be prior to cocking of the actuator 260 by the practitioner. As can be seen, the cannula hub 221 may be positioned at the distal end portion of the housing base 280. The torsional spring 264 may be in an unwound configuration. The torque converter 283 may be oriented such that the third arm 249 may be directed distally and the catch 239 of the first arm 245 is coupled with the post 255. The trigger 261 may be positioned in an intermediate position such that the distal end of the trigger first arm 236 is adjacent to a ramp 234.

FIG. 16A illustrates distal portions of the cannula 220 and the trocar 240 of the biopsy needle device 200 in the first configuration. As can be seen, a trocar bevel 256 may extend beyond the distal end of the cannula 220. A cannula bevel 225 may be located proximal to and adjacent to the trocar bevel 256.

FIG. 17 illustrates the relative locations of the torsional spring 264, the torque converter 283, the cannula hub 221, the trigger 261 and the flexible member 293 within the actuator 260 in the second configuration. The second configuration may be approximately halfway through cocking of the actuator 260 by the practitioner. As can be seen, the cannula hub 221 may be positioned at a proximal position. The torsional spring 264 may be in a partly wound configuration. The flexible member 293 may be partly uncoiled causing the torque converter 283 to rotate in the direction of the arrow. The torque converter 283 may be oriented such that the third arm 249 may be directed proximally and the catch 239 of the second arm 246 may be deflecting the post 255. The practitioner may feel slight resistance and/or hear a clicking sound as the second arm 246 passes and deflects the post 255. The trigger 261 may be positioned in an intermediate position.

FIG. 17A illustrates distal portions of the cannula 220 and the trocar 240 of the biopsy needle device 200 in the second configuration. The cannula bevel 225 may be displaced proximally and may be positioned proximal to the notch 257 such that the cannula 220 does not cover the notch 257.

FIG. 18 illustrates the relative locations of the torsional spring 264, the torque converter 283, the cannula hub 221 and the trigger 261 within the actuator 260 in the third configuration. The third configuration may be subsequent to cocking of the actuator 260. As can be seen, the cannula hub 221 may be positioned at a distal position. The torsional spring 264 may be in a fully wound configuration. The flexible member 293 may be fully uncoiled, causing the torque converter 283 to rotate in the direction of the arrow. The torque converter 283 may be oriented such that the third arm 249 may be directed distally and the catch 239 of the first arm 245 may be coupled with the post 255. The trigger 261 may be positioned in a proximal position.

FIG. 18A illustrates portions of the cannula 220 and the trocar 240 of the biopsy needle device 200 in the third configuration. As can be seen, the trocar bevel 256 may extend beyond the cannula bevel 225. The cannula bevel 225 may be displaced distally and may be positioned proximal to and adjacent to the trocar bevel 256.

FIG. 19 illustrates the relative locations of the torsional spring 264, the torque converter 283, the cannula hub 221, the trigger 261, and the flexible member 293 within the actuator 260 in the fourth configuration. The fourth configuration may occur as the actuator 260 is activated by the practitioner. As can be seen, the cannula hub 221 may be positioned at a distal position. The torsional spring 264 may be in a fully wound configuration. The flexible member 293 may be fully uncoiled. The torque converter 283 may be oriented such that the third arm 249 may be directed distally. The trigger 261 may be positioned in an fully distal position such that the distal end of the first arm 236 of the trigger 261 has engaged the ramp 234 and the flange 230 to deflect the post 255. The catch 239 of the first arm 245 of the torque converter 283 may decouple from the post 255, allowing the torque converter 283 to rotate, in the direction of the arrow, due to the spring force of the torsional spring 264.

FIG. 19A illustrates portions of the cannula 220 and the trocar 240 of the biopsy needle device 200 in the fourth configuration. As can be seen, the trocar bevel 256 may extend beyond the distal end of the cannula 220. The cannula bevel 225 may be located proximal to and adjacent to the trocar bevel 256.

FIG. 20 illustrates the relative locations of the torsional spring 264, the torque converter 283, the cannula hub 221, the trigger 261 and the flexible member 293 within the actuator 260 in the fifth configuration. The fifth configuration may be approximately halfway through activation of the actuator 260. As can be seen, the cannula hub 221 may be positioned at a proximal position. The torsional spring 264 may be in a partly unwound configuration. The flexible member 293 may be partly coiled around a portion of the torque converter 283. The torque converter 283 may be oriented such that the third arm 249 may be directed proximally and the catch 239 of the second arm 246 may rotate by the deflected post 255. It is to be understood that the rotation of the torque converter 183 is a continuous motion for approximately 360 degrees. That is, the rotational motion of the torque converter 183 does not stop after rotating 180 degrees. Rather, the torque converter 183 has continuous rotational movement for approximately 360 degrees. The fifth configuration represents an instant of time as the torque converter 283 continuously rotates. The trigger 261 may be positioned in the distal position.

FIG. 20A illustrates distal portions of the cannula 220 and the trocar 240 of the biopsy needle device 200 in the fifth configuration. The cannula bevel 225 may be displaced proximally and may be positioned proximal to the notch 257 such that the cannula 220 does not cover the notch 257. A tissue sample 259 may collapse or prolapse into the notch 257 and may at least partially fill the notch 257.

FIG. 21 illustrates the relative locations of the torsional spring 264, the torque converter 283, the cannula hub 221, the trigger 261, and the flexible member 293 within the actuator 260 in the sixth configuration. The sixth configuration may be subsequent to activation of the actuator 260 and severing of the tissue sample 259. As can be seen, the cannula hub 221 may be positioned at a distal position. The torsional spring 264 may be in a fully unwound configuration. The flexible member 293 may be fully coiled around a portion of the torque converter 283. The torque converter 283 may be oriented such that the third arm 249 may be directed distally and the catch 239 of the first arm 245 may be coupled with the post 255. The trigger 261 may be positioned in an intermediate position such that the distal end of the first arm 236 does not deflect the post 255.

FIG. 21A illustrates distal portions of the cannula 220 and the trocar 240 of the biopsy needle device 200 in the sixth configuration. As can be seen, the trocar bevel 256 may extend beyond the distal end of the cannula 220. The cannula bevel 225 may be displaced distally such that the cannula bevel 225 may cut or sever the tissue sample 259 from the lesion 258, and the cannula 220 may cover the notch 257 such that the tissue sample 259 may be retained within the notch 257. The distal end of the cannula 220 may be positioned proximal to and adjacent to the trocar bevel 256.

FIGS. 22 and 22A illustrates the relative locations of the torsional spring 264, the torque converter 283, the cannula hub 221, the trigger 261, and the flexible member 293 within the actuator 260 in the seventh configuration. The seventh configuration may allow the practitioner to extract the tissue sample 259 from the notch 257. As can be seen, the cannula hub 221 may be positioned at a proximal position. The torsional spring 264 may be in a partly wound configuration. The flexible member 293 may be partly uncoiled from a portion of the torque converter 283. The torque converter 283 may be oriented such that the third arm 249 may be directed proximally and the catch 239 of the second arm 246 may be coupled with the post 255. The trigger 261 may be positioned in an intermediate proximal position.

FIG. 22A illustrates distal portions of the cannula 220 and the trocar 240 of the biopsy needle device 200 in the seventh configuration. The cannula bevel 225 may be displaced proximally and may be positioned proximal to the notch 257 such that the cannula 220 does not cover the notch 257. The tissue sample 259 may be exposed such that it may be extracted from the notch 257 by the practitioner.

In some embodiments, the biopsy needle device 200 may permit the practitioner to perform the Core Needle Biopsy procedure. The location of the tissue or lesion to be biopsied within the patient may be identified utilizing known diagnosis techniques such as computed tomography, magnetic resonance imaging, x-ray, fluoroscopy, ultrasound, etc. The patient may be positioned and prepped for the Core Needle Biopsy procedure. The practitioner may obtain the sterilized biopsy needle device 200 configured with the desired trocar and cannula length and diameter and the desired length of notch 257 such that a desired sample length may be collected. The practitioner may prep the biopsy needle device 200 by cocking the actuator 260. The actuator 260 may be cocked by displacing the activation flange 250 and trigger 261 proximally. Proximal displacement of the trigger 261 pulls the flexible member 293, proximally resulting in uncoiling of the flexible member 293 from a portion of the torque converter 283. As the flexible member 293 uncoils the torque converter 283 is rotated and the torsional spring 264 is wound in a compressed configuration. The catch 239 of the first arm 245 of the torque converter 283 couples with the post 255 to hold the actuator 260 in a cocked configuration. The practitioner may insert the cannula 220 and the trocar 240 through the skin and into the lesion of the patient while holding the actuator 260 in a hand. Alternatively, the cannula 220 and the trocar 240 may be inserted into the lesion 258 of a patient utilizing an introducer cannula that was previously inserted into the patient. The practitioner may confirm the position of the cannula 220 and trocar 240 utilizing known techniques such as ultrasound, fluoroscopy, computed tomography, etc. The practitioner may activate the actuator 260 by applying a force to the activation flange 250, resulting in the first arm 236 of the trigger 261 deflecting the post 255 such that the catch 239 of the first arm 245 decouples from the post 255. The torsional spring 264 may unwind or decompress such that the torque converter 283 is rotated approximately 360 degrees in a continuous motion. The rotational movement of the torque converter 283 may be translated into initial proximal and then distal linear movement of the cannula hub 221 and cannula 220 through the linkage member 266. The torque converter 283 may rotate 180 degrees and the cannula hub 221 and cannula 220 may be displaced proximally to a maximum proximal position. The distal end of the cannula 220 may be positioned proximally of the notch 257 of the trocar 240. The notch 257 may be exposed to lesion tissue. A portion of the lesion tissue may collapse or prolapse into the notch 257. The torque converter 283 may complete the 360 degree rotation in a continuous motion, and the cannula hub 221 and the cannula 220 may be displaced to a distal position. The distal end of the cannula 220 may slide over the notch 257 and cut or sever the portion of the lesion or tissue sample 259 within the notch 257 from the surrounding lesion tissue. The tissue sample 259 may be captured and retained within the notch 257 by the cannula 220. The cannula 220 and the trocar 240 may be removed from the patient's tissue. The practitioner may extract the tissue sample 259 from the biopsy needle device 200 by displacing the trigger 261 proximally until the cannula 220 is positioned proximal of the notch 257 and the tissue sample 259 is exposed. The tissue sample 259 may be extracted from the biopsy needle device 200 and analyzed using known techniques.

As described above, in any of the embodiments described herein, the continuous motion of a portion of the actuator (such as actuators 160 and 260) may be configured to displace one or more portions of a biopsy needle device (such as devices 100 and 200) in a first direction, then in a second direction. For example, continuous rotation of a the torque converter (183, 283) in one rotational direction may be configured to displace the cannula (120, 220) from a proximal position, to a distal position, and back to a proximal position though continuous rotation of the torque converter (183, 283) in one direction of rotation.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A biopsy needle device, comprising:
    an elongate outer member comprising a distal end configured to sever a tissue sample;
    an elongate inner member disposed within the elongate outer member wherein the elongate inner member comprises a distal end configured to penetrate tissue and a notch configured to retain a tissue sample; and
    an actuator comprising:
        a torque converter configured such that a continuous motion of the torque converter 360 degrees in a first rotational direction displaces the outer member over the inner member from a distal position to a proximal position to the distal position as the actuator is cocked and a continuous motion of the torque converter 360 degrees in a second rotational direction displaces the outer member over the inner member from the distal position to the proximal position to the distal position as the actuator is activated;
        a linkage member that couples the torque converter to the outer member;
        a linear gear configured such that linear displacement of the linear gear is translated into rotational motion of the torque converter; and
        a trigger partially disposed within a housing of the biopsy needle device and engaged with the linear gear, the trigger is configured to cock the actuator and activate the actuator,
    wherein proximal linear movement of the trigger extends the trigger partially out of the housing which simultaneously moves the linear gear from a distal location to a proximal location within the housing which rotates the torque converter which causes linear movement of the elongate outer member relative to the elongate inner member via the linkage member, and
    wherein activation of the trigger causes distal linear movement of the trigger partially into the housing which simultaneously moves the linear gear from the proximal location to the distal location within the housing which causes linear movement of the elongate outer member relative to the elongate inner member via the linkage member.

2. The biopsy needle device of claim 1, wherein the actuator further comprises a circular gear configured to mesh with the linear gear and coupled to the torque converter;
    wherein the torque converter is coupled to the elongate outer member.

3. The biopsy needle device of claim 1, wherein the elongate inner member comprises a tube.

4. The biopsy needle device of claim 1, wherein the trigger further comprises a first hook configured to lock the linear gear in a cocked position.

5. The biopsy needle device of claim 4, wherein the trigger further comprises a second hook configured to displace the first hook away from the linear gear.

* * * * *